United States Patent

Wachtler et al.

Patent Number: 5,672,617
Date of Patent: Sep. 30, 1997

[54] MEDICAMENTS CONTAINING 1-THIOCARBAMOYL-5-HYDROXY-PYRAZOLES AND THEIR USE AS AGENTS FOR COMBATING SEPTIC SHOCK

[75] Inventors: Peter Wachtler, Köln; Lutz Heuer, Krefeld; Martin Kugler, Leichlingen; Heinrich Schrage, Krefeld, all of Germany

[73] Assignee: Bayer Aktiengesellschaft, Leverkusen, Germany

[21] Appl. No.: 598,878

[22] Filed: Feb. 9, 1996

Related U.S. Application Data

[63] Continuation-in-part of Ser. No. 286,080, Aug. 4, 1994, Pat. No. 5,510,365.

[30] Foreign Application Priority Data

| Aug. 11, 1993 | [DE] | Germany | 43 26 904.4 |
| Mar. 31, 1994 | [DE] | Germany | 44 11 243.2 |
| Apr. 28, 1994 | [DE] | Germany | 44 14 792.9 |
| Mar. 20, 1995 | [DE] | Germany | 195 10 058.1 |

[51] Int. Cl.$^6$ .................. A61K 31/415; C07D 231/20
[52] U.S. Cl. ...................... 514/407; 548/369.7
[58] Field of Search .................. 548/369.7; 514/407

[56] References Cited

U.S. PATENT DOCUMENTS

| 5,502,069 | 3/1996 | Sasse et al. | 514/404 |
| 5,510,365 | 4/1996 | Wachtler et al. | 514/407 |

FOREIGN PATENT DOCUMENTS

| 0515934 | 5/1992 | European Pat. Off. |

OTHER PUBLICATIONS

Chemical Abstracts, vol. 107, No. 17, Oct. 26, 1987, Abstract No. 154289r, K. Wegner et al.

Chemical Substances, 12th Collective Index vol. 106-115, 1987-1991 No. 78341CS.

Wegner et al Archiv Der Pharmazie Bd. 320, Nov. 2, 1987, pp. 108-114 Arch. Pharm. 316 (1983) 2-6.

Miyamoto et al. J. Pesticide Sci. 11, 205-212 (1986).

Tietze et al. Reactions and Syntheses, Thieme Verlag, 1981, pp. 153, 440.

Oikawa et al., J. Org. Chem. 43, 2087 (1978).

Derwent Abstract of JP 54-155,374 (1974).

Dewent Abstract of JP 54-119,031 (1979).

K. Wegner, Sci Pharm. 51, 167-172 (1983).

*Primary Examiner*—Johann Richter
*Assistant Examiner*—Laura R. Cross
*Attorney, Agent, or Firm*—Sprung Horn Kramer & Woods

[57] ABSTRACT

This application relates to new thiocarbamoyl compounds of the formula (I)

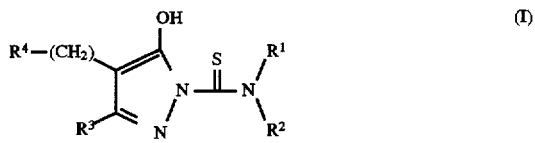

in which $R^1$, $R^2$, $R^3$ and $R^4$ have the meanings given in the description.

13 Claims, No Drawings

MEDICAMENTS CONTAINING 1-THIOCARBAMOYL-5-HYDROXY-PYRAZOLES AND THEIR USE AS AGENTS FOR COMBATING SEPTIC SHOCK

This application is a c-i-p of application Ser. No. 08/286,080, filed on Aug. 4, 1994, U.S. Pat. No. 5,510,365 allowed and a c-i-p of International Application PCT/EP94/02534 filed Jul. 29, 1994.

This invention relates to 1-thiocarbamoyl-5-hydroxypyrazole of the formula

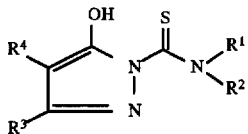

in which $R^1$ to $R^4$ are defined below. These compounds are useful as pharmaceuticals in treating septic shock and the consequences therefrom as well as in combatting undesirable microorganism, especially in protecting industrial material.

Thiocarbamoylpyrazoles represent a class of substances which is known in the protection of materials, since numerous representatives of this structural type have microbicidal properties and thus represent valuable material-protection agents, for example for the protection of paints or wood. This application is described in, for example, EP 515 934. In contrast, the use of thiocarbamoylpyrazoles as claimed in the present invention, in the pharmaceutical sector, especially for treating septic shock, has not been described hitherto.

The invention therefore relates to medicaments containing compounds of the general formula (I)

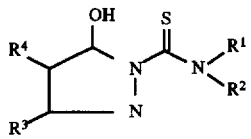

in which $R^1$ and $R^2$ independently of one another represent hydrogen, alkyl, cycloalkyl, alkenyl, aralkyl or aryl, the latter being unsubstituted or substituted with $C_{1-6}$-alkyl or halogen or $R^1$=H, $R^2$=$NH_2$, $R^3$ and $R^4$ independently of one another represent hydrogen or unsubstituted or substituted alkyl, alkenyl, alkinyl, cycloalkyl, cycloalkenyl, alkyl(cycloalkyl), alkenyl(cycloalkenyl), alkoxy, alkylthio, aralkoxy, aralkylthio, aralkyl, aryl, hetaryl, aryloxy, hetaryloxy, arylthio, hetarylthio, alkoxycarbonyl, alkoxycarbonylalkyl or cyanoalkyl, or $R^3$ and $R^4$ form a saturated or partially or completely unsaturated, unsubstituted or substituted ring, of 5 to 9 atoms in total, all of which are carbon atoms except for a maximum of two nitrogen, sulphur or oxygen atoms, or their metal complexes with metals such as, for example, iron, zinc, manganese, calcium, magnesium, potassium, sodium, lithium, lanthanum, platinum, gold and aluminium, and their physiologically acceptable salts with acids such as HCl, $HNO_3$, acetic acid, salicylic acid etc. "Substituted" in the definitions of $R^3$ and $R^4$ denotes substitution by from one to seven—but not more than the number of H atoms present in the unsubstituted case -atoms or groups of atoms selected from the group consisting of F, Cl, Br, I, $NO_2$, CN, O-alkyl, S-alkyl, alkyl, —$CO_2$-alkyl, cycloalkyl, aryl and $NO_2$.

The following definitions apply here and below:

Alkyl=straight-chain or branched alkyl having 1 to 18 C atoms, such as Me, Et, n-, i-propyl, n-, i-, s- and tert-butyl, n-, i- and-tert-pentyl, n-hexyl, n-octyl, n-nonyl, n-decyl, n-undecyl, n-dodecyl, n-tridecyl, n-tetradecyl, n-pentadecyl, n-hexadecyl, n-heptadecyl or n-octadecyl or their branched structural isomers.

These alkyl groups may be substituted by 1 to 15 halogen atoms, preferably chlorine and/or fluorine or CN.

The chain of C atoms may also be interrupted by 1 to 2 heteroatoms such as oxygen or sulphur, or groups of atoms such as N—Me, N—Et, —S(O), —$SO_2$, without its total number of atoms changing.

Alkenyl (+ alkinyl) is defined as for alkyl, but altered to the extent that at least one and not more than three C—C single bonds have been replaced by a C—C double (triple) bond. The number of C atoms is at least three and is increased by at least two C atoms for each additional double bond (triple bond) added.

Cycloalkyl and cycloalkenyl groups comprise cycloalkyl with preferably 3 (5) to 7 C atoms, for example cyclopropyl, cyclobutyl, cycloheptyl, cyclopentyl, cyclopentenyl, cyclohexenyl and cyclohexyl; preferred substituted cycloalkyl groups comprise cycloalkyl which is substituted by 1 to 3 $C_1$-$C_4$-alkyl groups or 1 to 3 halogen atoms, such as chlorine and/or fluorine, examples being methylcyclohexyl, dimethylcyclohexyl, 1,3,3-trimethylcyclohexyl and 3-chlorocyclohexyl. Alkyl(cycloalkyl) and alkyl (cycloalkenyl) groups preferably contain 1 to 6 C atoms in the straight-chain or branched alkyl moiety and 3 to 7 C atoms in the cycloalkyl/alkenyl moiety, and are in particular (1-cyclopentyl)methyl, (1-cyclopentenyl)methyl, (1-cyclohexenyl)methyl, (1-cyclohexyl)methyl and (1-cyclopropyl)methyl.

Alkoxycarbonyl represents straight-chain or branched alkoxycarbonyl having preferably 1 to 6 C atoms in the alkoxy radical, for example methoxycarbonyl, ethoxycarbonyl, n- and i-propoxycarbonyl, n-, i-, sec- and tert-butoxycarbonyl, and hexyloxycarbonyl. Analogous comments apply to the alkoxycarbonylalkyl groups.

Aralkyl preferably contains 1 to 6, in particular 1 to 4 C atoms in the straight-chain or branched alkyl moiety and preferably phenyl or naphthyl as the aryl moiety. Examples of such aralkyl groups include benzyl, α-methylbenzyl, α,α-dimethylbenzyl, 2-phenethyl, and α- and β-naphthylmethyl. These aralkyl radicals may carry 1 to 3 substituents from the series consisting of halogen (especially chlorine and/or fluorine), nitro, cyano or unsubstituted or halogenated $C_1$-$C_4$-alkyl or $C_1$-$C_4$-alkoxy, for example methyl, ethyl, trifluoromethyl, difluorochloromethyl, difluoromethyl, trichloromethyl, methoxy, ethoxy, trifluoromethoxy, difluorochloromethoxy and difluoromethoxy, or unsubstituted or halogenated $C_1$-$C_4$-alkylmercapto, for example methylmercapto, trifluoromethylmercapto or difluorochloromethylmercapto.

The term aryl denotes unsubstituted or substituted aryl having preferably 6 to 12 C atoms in the aryl moiety. Preferred examples include phenyl, biphenyl and naphthyl. The aryl groups may carry 1 to 3 substituents from the series consisting of halogen (especially chlorine and/or fluorine), $C_1$-$C_6$-alkyl, $C_1$-$C_6$-alkoxy or thioalkoxy, halogeno-$C_1$-$C_2$-alkyl (such as trifluoromethyl or difluoromethyl), cyano, nitro, $C_1$-$C_6$-alkoxycarbonyl or amino.

The term alkoxy denotes straight-chain or branched alkoxy having preferably 1 to 12, in particular 1 to 4 C atoms. Preferred examples include methoxy, ethoxy, n- and i-propoxy, n-, i-, sec- and tert-butoxy, pentoxy, hexoxy, heptoxy, octoxy, nonoxy and decoxy. The alkoxy groups may be substituted by 1 to 3 halogen atoms (Cl, F), preferably: O—$CF_3$, O—$CHF_2$, O—$CF_2$—O, O—$CF_2$—$CF_2$—O, O—CFCL—CFCL—O.

Alkylthio represents straight-chain or branched alkylthio having preferably 1 to 12 C atoms. Preferred examples include methylthio, ethylthio, n- and i-propylthio, n-, i-, sec- and tert-butylthio, n-pentylthio and its isomers such as 1-, 2- and 3-methyl-butylthio. The alkylthio groups may be substituted by 1 to 3 halogen atoms (preferably chlorine and/or fluorine); preferred examples of these are di- and trifluoromethylthio and difluorochloromethylthio.

Aralkoxy preferably contains 1 to 6 C atoms in the straight-chain or branched alkyl moiety and preferably phenyl as aryl moiety. Preferred examples are benzyloxy and phenethyloxy. The aralkoxy groups may be substituted by 1 to 3 halogen atoms (preferably chlorine and/or fluorine) or by a $C_1$–$C_4$-alkyl group.

Cyanoalkyl is as alkyl (1 to 6) but substituted by cyano, preferably terminally.

Hetaryl: furyl, thienyl, thiazolyl, pyrazolyl, pyrrolyl, imidazolyl, triazolyl, unsubstituted or with 1 to 2 halogen or with alkyl, alkoxy or thioalkoxy substituents.

Halogen: F, Cl, Br, I.

Aralkylthio preferably contains 1 to 6 C atoms in the straight-chain or branched alkyl moiety and preferably phenyl as aryl moiety. The preferred example is benzylthio. The aralkylthio groups may be substituted by 1 to 3 halogen atoms (preferably chlorine and/or fluorine) or by a $C_1$–$C_4$-alkyl group.

Aryloxy preferably contains 1 to 10 C atoms in the aryl moiety. Preferred examples are phenoxy and naphthoxy. The aryloxy groups may carry 1 to 3 substituents from the series consisting of halogen (preferably chlorine and/or fluorine), $C_1$–$C_4$-alkyl, halogeno-$C_1$–$C_2$-alkyl (such as di- and trifluoromethyl), cyano, nitro or amino.

Arylthio preferably contains 6 to 10 C atoms in the aryl moiety. Preferred examples are phenylthio and naphthylthio. The arylthio groups may carry the substituents listed under "aryloxy".

Preferred examples of 1, ω-$C_3$–$C_6$-alk(en)ylene radicals include 1,3-propylene, 1,4-butylene and 1,4-butadien(1,3)ylene.

Preferred compounds of the formula (I)

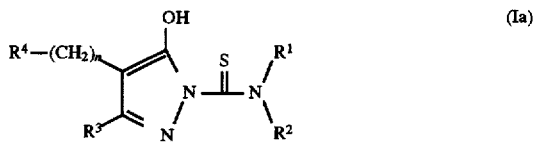

are those in which $R^1$ denotes hydrogen or unsubstituted or substituted alkyl, alkenyl or aryl, $R^2$ denotes hydrogen, $R^3$ denotes hydrogen or unsubstituted or substituted $C_1$–$C_8$-alkyl, cycloalkyl, alkenyl, aralkyl or aryl, and $R^4$ denotes hydrogen or unsubstituted or substituted alkyl, cycloalkyl, alkenyl, aralkyl or aryl.

Particularly preferred compounds of the formula (I) are those in which $R^1$ and $R^2$ denote hydrogen, $R^3$ denotes unsubstituted or substituted $C_1$–$C_6$-alkyl, aralkyl or aryl, and $R^4$ denotes hydrogen or unsubstituted or substituted alkyl, aralkyl or aryl.

Very particularly preferred compounds of the formula (I) are those in which $R^1$ and $R^2$ denote hydrogen, $R^3$ denotes unsubstituted or substituted $C_1$–$C_6$-alkyl or aralkyl, and $R^4$ denotes hydrogen, unsubstituted or substituted $C_1$–$C_6$-alkyl or aralkyl.

The compounds I to be used in accordance with the invention may be present as various tautomers (see below), including their tautomeric pyrazol-5-one form.

A preferred subset of the compounds of formula I are compounds of the formula (Ia)

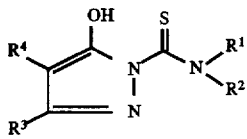

in which $R^1$, $R^2$ and $R^3$ in each case independently of one another represent hydrogen or methyl and $R^4$ represents cyclopentyl, cyclopentenyl, cyclohexyl or cyclohexenyl, n represents the number 0 or 1, and metal salt complexes and acid addition products thereof.

Particularly preferred compounds of the formula (Ia) are those in which $R^1$, $R^2$ and $R^3$ represent hydrogen, and in particular the compound of the formula (Ia) in which $R^1$, $R^2$ and $R^3$ represent hydrogen and $R^4$ represents cyclohexyl.

Some of the compounds of formula I which are used in accordance with the invention as well as processes for their preparation, are known. For instance, published Japanese Patent Applications 79/115 374 and 79/119 031 describe 3-mono and 3,4-disubstituted 1-thiocarbamoyl-5-hydroxy-pyrazoles which are active against plant diseases. They are said in particular to possess fungicidal action; cf. also J. Pesticide Sci. 11, 205–212 (1986). The compound of formula (Ia) are nvoel as well as their utility as microbiocides.

Arch. Pharm. 316 (1983) 2–6 and Sci. Pharm. 51 (2) (1982) 167–172 disclose 4-mono- and 3,4-disubstituted 1-thiocarbamoyl-5-hydroxy-pyrazoles which are used as intermediates in the production of preparations having an antihistamine action.

EP 515 934 claims the use of 1-thiocarbamoyl-5-hydroxy-pyrazoles as material-protection agents.

To the extent that the compounds are still new, they can be prepared by analogy with the known preparation methods. Conventionally, an α-formylacetic ester or an α-formylacetamide or a β-ketoacetic ester or a β-ketoacetamide is reacted with a substituted or unsubstituted thiosemicarbazide. This condensation reaction takes place in accordance with the following equation (demonstrated using ethyl β-ketoacetate as the β-diketo starting product):

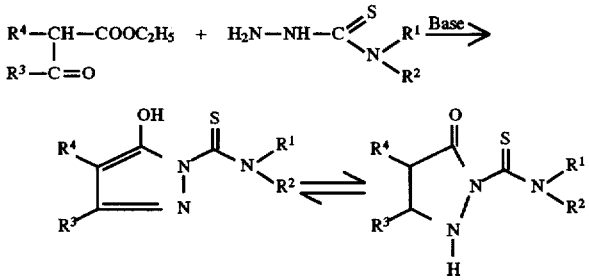

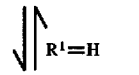 

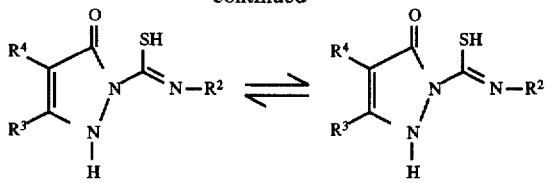

In the above formula, the substituents $R^1$ to $R^4$ have the definitions given above with respect to the compounds of the formula I.

0.8 to 1.0 mol of thiosemicarbazide is preferably reacted per mole of α-formylacetic acid derivative or per mole of β-diketo compound.

To facilitate the ring closure reaction, it is advantageous to add bases such as sodium hydroxide, potassium hydroxide or potassium tert-butylate. The base is preferably added in an amount approximately equivalent to the α-formylacetic acid derivative or the β-diketo compound.

The condensation may, if desired, be carried out in the presence of a solvent; solvents which have proved to be particularly suitable are alcohols such as ethanol or aromatic hydrocarbons such as toluene.

The condensation reaction can be carried out within a relatively large temperature range. For the first step of thiosemicarbazone formation, the temperatures may be from 20° to 110° C., preferably between 60° and 90° C. The cyclocondensation reaction, which takes place after the addition of base, can be carried out at temperatures from 20° to 100° C., preferably from 20° to 40° C. Since in many cases the addition of base is an exothermic procedure, cooling may be necessary in this step of the reaction.

The 1-thiocarbamoyl-5-hydroxy-pyrazoles can be isolated from the reaction mixtures by known methods. The general procedure is to free the reaction mixtures from solvent and to treat the residue with aqueous hydrochloric acid. The pyrazoles which precipitate in this procedure are separated off by filtration with suction. However, it is also possible to pour the reaction mixture directly into a large excess of dilute hydrochloric acid and to filter off the precipitated pyrazoles.

The starting compounds required for the preparation of the compounds I to be used in accordance with the invention, these starting compounds being namely the α-formylacetic esters or amides and the unsubstituted or α-substituted β-ketoacetic esters or amides, and the unsubstituted or substituted thiosemicarbazides, are either known compounds or can be prepared in analogy to known compounds by methods described earlier. In this context the following methods are useful: Tietze, Eicher, Reaktionen und Synthesen [Reactions and Syntheses], Thieme Verlag 1981, p. 153, 440; Oikawa, J. Org. Chem., 43, 2087 (1978).

As already mentioned above, some of the compounds I to be used in accordance with the invention are new. In addition to the compounds of formula (Ia) this invention also relates furthermore to compounds of the formula (IIa)

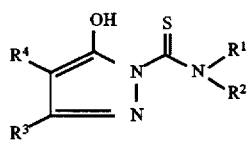

in which $R^1$ and $R^2$ denote H, alkenyl or aryl, with the proviso that $R^1$ and $R^2$ are not simultaneously hydrogen, and $R^3$ and $R^4$ have the definitions given above with regard to the compounds of the formula (I).

The compounds of the formula (Ia) are obtained by reacting formic acid derivatives of the formula (II)

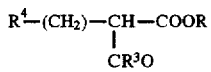

in which $R^3$ and $R^4$ have the abovementioned meanings and R represents methyl, ethyl, n- or i-propyl or n-, i-, s- or t-butyl, with thiosemicarbazides of the formula (III)

$$NH_2-NH-CS-NR^1R^2 \qquad (III)$$

if appropriate in the presence of a diluent or solvent and/or a base.

0.8 to 1.0 mol of thiosemicarbazide is preferably employed here per mole of α-formylacetic acid derivative.

Sodium hydroxide, potassium hydroxide or potassium tert-butylate are preferably added as bases, preferably in approximately equimolar amounts.

Possible solvents or diluents are, above all, alcohols, such as ethanol, or aromatic hydrocarbons, such as toluene.

The condensation reaction is carried out within a relatively wide temperature range. The thiosemicarbazone formation, which proceeds first, is carried out at temperatures from 20° to 110° C., preferably 60° to 90° C. The cyclocondensation reaction which proceeds after addition of the base is carried out at temperatures from 20° to 100° C., preferably 20° to 40° C.

The 1-thiocarbamoyl compounds of the formula (Ia) according to the invention are isolated from the reaction mixtures by known methods. A procedure is in general followed in which the reaction mixtures are freed from the solvent and the residue is treated with aqueous hydrochloric acid. The pyrazoles obtained by this procedure are separated off by filtration with suction. However, it is also possible for the reaction mixture to be poured directly into a large excess of dilute hydrochloric acid and for the pyrazoles which separate out as a precipitate to be filtered off.

The thiosemicarbazides of the formula (III) are known or are obtainable by generally known preparation processes.

The formyl acid derivatives of the formula (II) are new and the Application likewise relates to these.

They are obtained by formylating esters of the formula (IV)

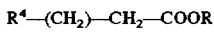

in which $R^4$ and R have the abovementioned meaning, with bases, such as, for example, NaH, in solvents or diluents, such as, for example, cyclohexane and dimethylformamide, with amine acid esters, such as methyl or ethyl esters.

The formyl acid derivatives of the formula (II) are also obtained by hydroformylating corresponding α,β-unsaturated esters by generally known methods, as described, for example, in EP-417,597 or DE-2,643,205.

The active compounds of the formula (Ia) and the compositions comprising them have a potent microbicidal action and can be employed in practice for combating undesirable microorganisms. The active compounds of the formula (Ia) and the compositions according to the invention are suitable for protecting industrial materials against attack and destruction by undesirable microorganisms.

Industrial materials in the present connection are to be understood as non-living materials which have been prepared for use in industry. For example, industrial materials which are to be protected by active compounds according to the invention against microbial change or destruction can be adhesives, sizes, paper and card, textiles, leather, wood, paints and articles of plastic, cooling lubricants and other materials which may be attacked or destroyed by microorganisms. Components of production plants, for example cooling water circulations, which may be impaired by multiplication of microorganisms may also be mentioned in the context of the materials to be protected. Industrial materials which may be mentioned in the context of the present invention are preferably adhesives, sizes, papers and cards, leather, wood, paints, cooling lubricants and heat transfer liquids, particularly preferably paints.

Examples which may be mentioned of microorganisms which may cause degradation of or a change in the industrial materials are bacteria, fungi, yeasts, algae and slime organisms. The active compounds and compositions according to the invention preferably act against fungi, in particular moulds, wood-discolouring and wood-destroying fungi (Basidiomycetes), and against slime organisms and algae.

Microorganisms of the following genera may be mentioned as examples:

Alternaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

Depending on their particular physical and/or chemical properties, the active compounds of the formula (Ia) can be converted into customary formulations, such as solutions, emulsions, suspensions, powders, foams, pastes, granules, aerosols and very fine capsules in polymeric substances.

These formulations are produced in a known manner, for example by mixing the active compounds with extenders, that is liquid solvents, liquefied gases under pressure and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide or dimethyl sulphoxide, as well as water; by liquefied gaseous extenders or carriers are meant liquids which are gaseous at ambient temperature and under atmospheric pressure, for example aerosol propellents, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The active compounds of the formula (Ia) according to the invention are preferably employed for protecting paint films against attack and destruction by undesirable microorganisms.

Paint film in the present connection is to be understood as meaning a coating produced from paints on a substrate. The paint film can have penetrated to a greater or lesser extent into the substrate. It can comprise one or more layers and be produced by processes such as brushing, spraying, dipping, flooding or similar processes.

The compounds of the formulae (Ia) are incorporated into the paints or into precursors for the preparation of the paints by customary methods, for example by mixing the active compounds with the other components.

Paints according to the invention therefore comprise, in addition to at least one fungicidal active compound of the formula (Ia), generally customary paint film components in, for example, liquid, pasty or pulverulent form, such as, for example, Colouring agents, such as pigments or dyestuffs, preferably pigments. Examples which may be mentioned are titanium dioxide, zinc oxide and iron oxide.

Binders, such as, for example, oxidatively drying alkyd resins, vinyl polymers and vinyl copolymers, acrylic polymers and acrylic copolymers, powdered plastics, novolaks, amino resins, polyester resins, epoxy resins, silicone resins, isocyanate resins vinyl polymers and vinyl copolymers, acrylic polymers and acrylic copolymers and other binders which can be used in waterdilutable paints are preferred.

In addition, if appropriate, the paint films comprise the following additives fillers, such as, for example, baryte, calcite, dolomite and talc, solvents, such as, for example, alcohols, ketones, esters, glycol ethers and aliphatic and aromatic hydrocarbons, and thickening and thixotropic agents, dispersing and wetting agents, drying agents, skin prevention agents, flow agents, antifoam agents, corrosion inhibitors, UV absorbers, fragrances, antistatics and antifreezes.

The following paints or precursors for the preparation of paints may be mentioned as preferred:

Sizes and adhesives based on the known animal, vegetable or synthetic raw materials.

Plastics dispersions, such as latex dispersions or dispersions based on other polymers.

Starch solutions, dispersions or slurries or other products prepared on a starch basis, such as, for example, printing thickeners.

Slurries of other raw materials, such as coloured pigments (for example iron oxide pigments, carbon black pigments, titanium dioxide pigments) or slurries of fillers, such as kaolin or calcium carbonate.

Concrete additives, for example based on molasses or ligninsulphonates.

Bitumen emulsions.

Precursors and intermediates of the chemical industry, for example in the production and storage of dyestuffs.

Inks or water colours.

Emulsion paints for the paint industry.

Layers and finishes.

The activity and the action spectrum of the active compounds of the formulae (I) or the compositions which can be prepared therefrom, precursors or quite generally formulations can be increased if, where appropriate, other antimicrobially active compounds, fungicides, bactericides, herbicides, insecticides or other active compounds are added to increase the action spectrum or achieve particular effects, such as, for example, additional protection from insects. These mixtures can have a broader action spectrum than the compounds according to the invention.

Synergistic effects are obtained here in many cases, i.e. the activity of the mixture is greater than the activity of the individual components. Particularly favourable mixing partners are, for example, the following compounds:

Triazoles, such as:

amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, metconazole, epoxyconazole, paclobutrazol, penconazole, propioconazole, (±)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and metal salts and acid adducts thereof.

Imidazoles, such as:

imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides, such as 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one and metal salts and acid adducts thereof.

Methyl (E)-2-[2-[6-(2-cyanophenoxy)pydmidin-4-yloxy)]phenyl]3-methoxyacrylate, methyl (E)-2-[2-[6-(2-thioamidophenoxy)pyrimidin-4-yloxy)]phenyl]-3-methoxyacrylate, methyl (E)-2-[2-[6-(2-fluorophenoxy)pyrimidin-4-yloxy)]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenylsulphonyloxy)phenoxy]phenyl]-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethylbenzoyl)pyrrol-1-yl]-3-methoxyacrylate, methyl (E)-2-[2-(3-methoxyphenoxy)phenyl]-3-methoxyacrylate, methyl (E)-2-[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl(E)-2-(2-[3-(alpha-hydroxybenzyl)phenoxy]phenyl)-3-methoxyacrylate, methyl (E)-2-( 2-(4-phenoxypyridin-2-yloxy)phenyl)-3-methoxyacrylate, methyl (E)-2-[2-(3-n-propyloxyphenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxy)phenoxy]phenyl]-3-methoxyacrylate, methyl (E)-2-[2-(3-ethoxyphenoxy)-phenyl]-3-methoxyacrylate, methyl (E)-2-[2-(4-tert-butylpyridin-2-yloxy)phenyl]-3-methoxyacrylate, methyl (E)-2-[2-[3-(3-cyanophenoxy)phenoxy]phenyl]-3-methoxyacrylate, methyl (E)-2-[2-(3-methylpyridin-2-yloxymethyl)phenyl]-3-methoxyacrylate, methyl (E)-2-[2-[6-(2-methylphenoxy)pyrimidin-4-yloxy]phenyl]-3-methoxyacrylate, methyl (E)-2-[2-(5-bromopyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, (E),(E)methyl-2-[2-(5,6-dimethylpyrazin-2-ylmethyloximinomethyl)phenyl]-3-methoxyacrylate, (E)-methyl-2-{2-[6-(6-methylpyridin-2-yloxy)pyrimidin-4-yloxy]phenyl}-3-methoxyacrylate, (E),(E)methyl-2-{2-(3-methoxyphenyl)methyloximinomethyl]phenyl}-3-methoxyacrylate, (E)methyl-2-{2-(6-(2-azidophenoxy)-pyrimidin-4-yloxy]phenyl}3-methoxyacrylate, (E),(E) methyl-2-{2-[6-phenyl-pyrimidin-4-yl)-methyloximinomethyl]phenyl}-3-methoxyacrylate, (E),(E) methyl-2-{2-[(4-chlorophenyl)-methyloximinomethyl] phenyl}-3-methoxyacrylate, (E)methyl-2-{2-[6-(2-n-propylphenoxy)-1,3,5-triazin-4-yloxy]phenyl}-3-methoxyacrylate, (E),(E)methyl-2-{2-[(3-nitrophenyl)methyloximinomethyl]phenyl}-3-methoxyacrylate;

Succinate dehydrogenase inhibitors, such as:

fenfuram, furcarbanil, cyclafluramid, furmecyclox, seedvax, metsulfovax, pyrocarbolid, oxycarboxin, Shirlan, mebenil (mepronil), benodanil, flutolanil (moncut);

naphthalene derivatives, such as terbinafine, naftifine, butenafine, 3-chloro-7-(2-aza-2,7,7-trimethyl-oct-3-en-5-ine);

sulfenamides, such as dichlofluanid, tolylfluanid, folpet, fluorfolpet; captan, captofol;

benzimidazoles, such as carbendazim, benomyl, furathiocarb, fuberidazole, thiophonatemethyl, thiabendazole or salts thereof;

morpholine derivatives, such as tridemorph, fenpropimorth, falimorph, dimethomorph, dodemorph, aldimorph, fenpropidin and its arylsulphonic acid salts, such as, for example, p-toluenesulphonic acid and p-dodecylphenyl-sulphonic acid;

dithiocarbamates, cufraneb, ferbam, mancopper, mancozeb, maneb, metam, metiram, thiram zeneb, ziram;

benzothiazoles, such as 2-mercaptobenzothiazole;

benzamides, such as 2,6-dichloro-N-(4-trifluoromethylbenzyl)-benzamide;

boron compounds, such as boric acid, boric acid esters, borax;

formaldehyde and compounds which split off formaldehyde, such as benzyl alcohol mono-(poly)-hemiformal, oxazolidine, hexa-hydro-S-triazine, N-methylolchloroacetamide, paraformaldehyde, nitropyrin, oxolic acid, tecloftalam;

tris-N-(cyclohexyldiazeniumdioxy)-aluminium, N-(cyclo-hexyldiazeniumdioxy)-tributyltin and K salts, bis-N-(cyclohexyldiazeniumdioxy)-copper;

N-methylisothiazolin-3-one, 5-chloro-N-methylisothiazolin-3-one, 4,5-dichloro-N-octylisothiazolin-3-one, N-octyl-isothiazolin-3-one, 4,5-trimethyleneisothiazolinone, 4,5-benzisothiazolinone and N-methylolchloroacetamide;

aldehydes, such as cinnamaldehyde, formaldehyde, glutarodialdehyde, β-bromocinnamaldehyde;

thiocyanates, such as thiocyanatomethylthiobenzothiazole, methylene bisthiocyanate and the like;

quaternary ammonium compounds, such as benzyldimethyltetradecylammonium chloride, benzyldimethyldodecylammonium chloride, didecyldimethaylammonium chloride;

iodine derivatives, such as diiodomethyl-p-tolylsulphone, 3-iodo-2-propinyl alcohol, 4-chlorophenyl-3-iodopropargylformal, 3-bromo-2,3-diiodo-2-propenylethyl carbamate, 2,3,3-triiodoallyl alcohol, 3-bromo-2,3-diiodo-2-propenyl alcohol, 3-iodo-2-propinyl-n-hexyl carbamate, 3-iodo-2-propinyl-cyclohexyl carbamate, 3-iodo-2-propinylphenyl carbamate;

phenol derivatives, such as tribromophenol, tetrachlorophenol, 3-methyl-4-chlorophenol, 3,5-dimethyl-4-chlorophenol, phenoxyethanol, dichlorophen, o-phenylphenol, m-phenylphenol, p-phenylphenol, 2-benzyl-4-chlorophenol and alkali metal and alkaline earth metal salts thereof;

microbicides having an activated halogen group, such as chloroacetamide, bronopol, bronidox, tectamer, such as 2-bromo-2-nitro-1,3-propanediol, 2-bromo-4'-hydroxy-acetophenone, 2,2-dibromo-3-nitrilopropionamide, 1,2-dibromo-2,4-dicyanobutane, β-bromo-β-nitrostyrene;

pyridines, such as 1-hydroxy-2-pyridinethione (and its Na, Fe, Mn, Zn salts), tetrachloro-4-methylsulphonylpyridine, pyrimethanol, mepanipyrim, dipyrithione and 1-hydroxy-4-methyl-6-(2,4,4-trimethylpentyl)-2(1H)-pyridine;

metal soaps, such as the naphthenate, octoate, 2-ethylhexanoate, oleate, phosphate, benzoate of tin, copper, zinc;

metal salts, such as copper hydroxycarbonate, sodium dichromate, potassium dichromate, potassium chromate, copper sulphate, copper chloride, copper borate, zinc fluorosilicate, copper fluorosilicate;

oxides, such as tributyltin oxide, $Cu_2O$, CuO, ZnO;

dialkyldithiocarbamates, such as the Na and Zn salts of dialkyldithiocarbamates, tetramethylthiuram disulphide, potassium N-methyl-dithiocarbamate;

nitriles, such as 2,4,5,6-tetrachloroisophthalodinitrile, disodium cyano-dithioimidocarbamate;

quinolines, such as 8-hydroxyquinoline and Cu salts thereof;

mucochloric acid, 5-hydroxy-2(5H)-furanone;

4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazin-2-thione, N-(2-p-chlorobenzoylethyl)-hexaminium chloride, potassium N-hydroxymethyl-N"-methyl-dithiocarbamate, 2-oxo-2-(4-hydroxy-phenyl)acethydroximic acid chloride, phenyl-(2-chloro-cyano-vinyl)sulphone, phenyl-(1,2-dichloro-2-cyano-vinyl)sulphone;

Ag, Zn or Cu-containing zeolites, by themselves or included in polymeric active compounds.

Mixtures which are especially preferred are those with azaconazole, bromuconazole, cyproconazole, dichlobutrazol, diniconazole, hexaconazole, metaconazole, penconazole, propiconazole, tebuconazole, methyl (E)-methoximino[α-(o-tolyloxy)-o-tolyl)]acetate, methyl (E)-2-{2-[6-(2-cyanophenoxy)pyrimidin-4-yl-oxy]phenyl}-3-methoxyacrylate, methfuroxam, carboxin, fenpiclonil, 4-(2,2-difluoro-1,3-benzodioxol-4-yl)-1H-pyrrole-3-carbonitrile, butenafine, imazalil, N-methyl-isothiazolin-3-one, 5-chloro-N-methylisothiazolin-3-one, N-octylisothiazolin-3-one, benzisothiazolinone, N-(2-hydroxypropyl)-amino-methanol, benzyl alcohol (hemi)-formal, glutaraldehyde, omadine, dimethyl dicarbonate.

Mixtures having a good action are furthermore also prepared with the following active compounds:

Fungicides:

acypetacs, 2-aminobutane, ampropylfos, anilazine, benalaxyl, bupirimate, chinomethionate, chloroneb, chlozolinate, cymoxanil, dazomet, diclomezine, dichloram, diethofencarb, dimethirimol, diocab, dithianon, dodine, drazoxolon, edifenphos, ethirimol, etridiazole, fenarimol, fenitropan, fentin acetate, fentin hydroxide, ferimzone, fluazinam, fluromide, flusulfamide, flutriafol, fosetyl, fthalide, furalaxyl, guazatine, hymexazol, iprobenfos, iprodione, isoprothiolane, metalaxyl, methasulfocarb, nitrothalisopropyl, nuarimol, ofurace, oxadiyl, perflurazoate, pencycuron, phosdiphen, pimaricin, piperalin, procymidone, propamocarb, propineb, pyrazophos, pyrifenox, pyroquilon, quintozene, tar oils, tecnazene, thicyofen, thiophanate-methyl, tolclofos-methyl, triazoxide, trichlamide, tricyclazole, triforine, vinclozolin.

Insecticides:

phosphoric acid esters, such as azinphos-ethyl, azinphos-methyl, α-1(4-chlorophenyl)-4-(O-ethyl, S-propyl) phosphoryloxy-pyrazole, chlorpyrifos, coumaphos, demeton, demeton-S-methyl, Diazinon, dichlorvos, dimethoate, ethoate, ethoprophos, etrimfos, fenitrothion, fenthion, heptenophas, parathion, parathion-methyl, phosalone, phoxim, pirimiphos-ethyl, pirimiphos-methyl, profenofos, prothiofos, sulfprofos, triazophos and trichlorphon;

carbamates, such as aldicarb, bendiocarb, α-2-(1-methylpropyl)-phenylmethyl carbamate, butocarboxim, butoxycarboxim, carbaryl, carbofuran, carbosulfan, cloethocarb, isoprocarb, methomyl, oxamyl, pirimicarb, promecarb, propoxur and thiodicarb;

organosilicon compounds, preferably dimethyl(phenyl) silyl-methyl-3-phenoxybenzyl ethers, such as dimethyl-(4-ethoxyphenyl)-silylmethyl-3-phenoxybenzyl ether or (dimethylphenyl)-silyl-methyl-2-phenoxy-6-pyridylmethyl ethers, such as, for example, dimethyl-(9-ethoxy-phenyl)-silylmethyl-2-phenoxy-6-pyridylmethyl ether or [(phenyl)-3-(3-phenoxyphenyl) -propyl](dimethyl)-silanes, such as, for example, (4-ethoxyphenyl)-[3-(4-fluoro-3-phenoxyphenyl-propyl]dimethyl-silane, silafluofen; pyrethroids, such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoromethylvinyl)-cyclopropanecarboxylate, fenpropathrin, fenfluthrin, fenvalerate, flucythrinate, flumethrin, fluvalinate, permethrin, resmethrin and tralomethrin;

nitroimines and nitromethylenes, such as 1-[(6-chloro-3-pyridinyl)-methyl]-4,5-dihydro-N-nitro-1H-imidazol-2-amine (imidacloprid), N-[(6-chloro-3-pyridyl)-methyl-]$N^2$-cyano-$N^1$-methylacetamide (NI-25);

abamectin, AC 303, 630, acephate, acrinathrin, alanycarb, aldoxycarb, aldrin, amitraz, azamethiphos, *Bacillus thuringiensis*, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulfuryl fluoride, tar oils, teflubenzuron, tefluthrin, temephos, terbufos, tetrachlorvinphos, tetramethrin, O-2-tertbutylpyrimidin-5-yl-o-isopropyl-phosphorothiate, thiocyclam, thiofanox, thiometon, tralomethrin, triflumuron, trimethacarb, vamidothion, Verticillium lacanii, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulphide, carbophenothion, cartap, chinomethionat, chlordane, chlorfenvinphos, chlorfluazuron, chlormephos, chloropicrin, chlorpyrifos, cyanophos, beta-cyfluthrin, alpha-cypermethrin, cyophenothrin, cyromazine, dazomet, DDT, demeton-S-methylsulphon, diafenthiuron, dialifos, dicrotophos, diflubenzuron, dinoseb, deoxabenzofos, diaxacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathione, iodfenphos, kadethrin, lindane, malathion, mecarbam, mephosfolan, mercurous, chloride, metam, Metarthizium, anisopliae, methacrifos, methamidophos, methidathion, methiocarb, methoprene, methoxychlor, methyl isothiocyanate, metholcarb, mevinphos, monocrotophos, naled, neodiprion sertifer NPV, nicotine, omethoate, oxydemeton-methyl, pentachlorophenol, petroleum oils, phenothrin, phenthoate, phorate.

Molluscicides:

fentin acetate, metaldehyde, methiocarb, niclosamide, thiodicarb, trimethacarb.

Algicides:

copper sulphate, dichlororphen, endothal, fentin acetate, quinoclamine.

Herbicides:

acetochlor, acifluorfen, aclonifen, acrolein, alachlor, alloxydim, ametryn, amidosulfuron, amitrole, ammonium sulfamate, anilofos, asulam atrazine, aziptrotryne, benazolin, benfluralin, benfuresate, bensulfuron, bensulfide, bentazone, benzofencap, benzthiazuron, bifenox, bilanafos, borax, dichlorprop, dichlorprop-P, diclofop, diethatyl, difenoxuron, difenzoquat, diflufenican, dimefuron, dimepiperate, dimethachlor, dimethametryn, dimethipin, dimethylarsinic acid, dinitramine, dinoseb, dinoseb, dinoseb acetate, dinoseb, bromacil, bromobutide, bromofenoxim, bromoxynil, butachlor, butamifos, fuenachlor, butralin, butylate, carbetamide, CGA 184927, chlormethoxyfen, chloramben, chlorbromuron, chlorbutam, chlorfurenol, chloridazon, chlorimuron, chlornitrofen, chloroacetic acid, achloropicrin, chlorotoluron, chloroxuron, chlorprepham, chlorsulfuron, chlorthal, chlorthiamide, cinmethylin, cinofulsuron, clethodim, clomazone, clomeprop, clopyralid, cyanamide, cyanazine, dinoseb acetate, dinoterb, diphenamide, dipropetryn, diquat, dithiopyr, diduron, DNOC, PPX-A 788, DPX-E96361, DSMA, eglinazine, endothal, EPTC, esprocarb, ethalfluralin, ethidimuron, ethofumesate, fenoxaprop, fenoxaprop-P, fenuron, flamprop, flamprop-M, flazasulfuron, fluazifop, fluazifop-P, fluchloralin, flumeturon, fluorocgycofen, fluoronitrofen, flupropanate, flurenol, fluridone, flurochloridone, fluoroxypyr, cycloate, cycloxydim, 2,4-D, daimuron, dalapon, dazomet, 2,4-DB, desmedipham, dsemetryn, dicamba, dichlorbenil, isoproturon, isouron, isoxaben, isoxapyrifop, lactofen, lenacil, linuron, LS830556, MCPA, MCPA-thioethyl, MCPB, mecoprop, mecoprop-P, mefenacet, mefluidide, metam, metamitron, metazachlor, methabenzthiazuron, methazole, methoproptryne, methyldymron, methyl isothiocyanate, metobromuron, fomosafen, fosamine, furyloxyfen, glufosinate, glyphosate, haloxyfop, hexazinone, imazamethabenz, imazapyr, imazaquin, imazethapyr, ioxynil, isopropalin, propyzamide, prosulfocab, pyrazolynate, pyrazolsulphuron, pyrazoxyfen, pyributicarb, pyridate, quinclorac, quinmerac, quinocloamine, quizalofop, quzizalofop-P, S-23121, sethoxydim, sifuron, simazine, semitryn, SMY 1500, sodium chlorate, sulfometuron, tar oils, TCA, metolachlor, metoxuron, metribzin, metsulfuron, molinate, monalide, monolinuron, MSMA, naproanilide, napropamide, naptalam, neburon, nicosulphuron, nipyraclofen, norflurazon, orbencarb, oaryzalin, oxadiazon, oxyfluorfen, paraquat, pebulate, pendimethalin, pentachlorophenol, pentaochlor, petroleum oils, phenmedipham, picloram, piperophos, pretilachlor, primisulfuron, prodiamine, proglinazine, propmeton, prometryn, propachlor, tebutam, tebuthiuron, terbacil, terbumeton, terbuthylazine, terbutryn, thiazafluoron, thifensulfuron, thiobencarb, thiocarbazil, tioclorim, tralkoxydim, tri-allate, triasulphuron, tribenzuron, triclopyr, tridiphane, trietazine, trifluralin, IBI-C4874 vernolate, propanil, propaquizafop, propazine, propham.

The weight ratios of the active compounds in these active compound combinations can be varied within relatively wide ranges.

The active compound combinations preferably comprise the active compound of the formula (I) to the extent of 0.1 to 99.9%, in particular to the extent of 1 to 75%, particularly preferably 5 to 50%, the remainder to 100% being made up by one or more of the abovementioned partners in the mixture.

The microbicidal agents or concentrates used for protection of industrial materials comprise the active compound or the active compound combination in a concentration of 0.01 and 95% by weight, in particular 0.1 to 60% by weight.

The use concentrations of the active compounds to be used or of the active compound combinations depends on the nature and the occurrence of the microorganisms to be combated and on the composition of the material to be protected. The optimum amount employed can be determined by test series. The use concentrations are in general in the range from 0.001 to 5% by weight, preferably from 0.05 to 1.0% by weight, based on the material to be protected.

The active compounds or compositions according to the invention advantageously allow the microbicidal agents hitherto available to be replaced by more effective agents. They show a good stability and advantageously have a broad action spectrum.

The following examples serve to illustrate the invention. The invention is not limited to the examples.

MATERIALS AND METHODS

Endotoxic shock $B_6D_2F_1$ mice are pretreated with galactosamine (600 mg/kg) and endotoxic shock is initiated with LPS (S. abortus equi, 0.01 µg/mouse). The mice die 8 to 24 hours after administration of LPS. The substances are given intravenously, subcutaneously, intraperitoneally or orally one hour before administration of LPS.

TNFα activity in serum

NMRI mice are treated with the substances one hour before administration of LPS. 1.5 hours after initiating the shock, blood samples are taken from which serum is obtained and the serum samples are frozen at −70° C. until testing. The TNFα serum activity is determined by a modified method of Espevik et al. (J. Immunol. Methods 956:99, 1986), which is based on the cytolysis of TNFα-sensitive cells (WEHI-164/13): 5×10⁴ cells are incubated overnight in FCS-RPMI medium in 96-well plates. Subsequently the cells are incubated with the serum samples in various concentrations (overnight at 37° C. and 7% $CO_2$). The control sera employed are from untreated mice or from mice treated only with LPS. After the incubation steps the cells are stained.

Action of thiocarbamoylpyrazolones

The action of thiocarbamoylpyrazolones was demonstrated after a single intravenous, subcutaneous, intraperitoneal or oral administration.

| Example | Inhibition of endotoxic shock in mice (mortality) |
|---|---|
| 2/005 | |
| 2/007 | |
| 2/011 | |
| 2/012 | ≦10 mg/kg iv |
| 2/013 | |
| 3/035 | |
| 4/004 | |
| 10/007 | |

The prevention of mortality by the thiocarbamoylpyrazolones is correlated with the inhibition of TNFα activity in serum (Examples: 3/035 and 2/036 at 10 mg/kg).

EXAMPLES

No. 7 from Table 1 (1/007)

10.3 g (0.06 mol) of ethyl α-formyl-hexanoate and 5.5 g (0.06 mol) of thiosemicarbazide are placed in 200 ml of ethanol and stirred at 80° C. for 3 hours.

The mixture is then brought to room temperature and 6.9 g of potassium tert-butylate are added with stirring, after which stirring is continued at room temperature for 4 hours. The contents of the flask are then stirred into a mixture of 800 ml of water and 50 ml of conc. hydrochloric acid, and the resulting precipitate is filtered off with suction. The product is washed thoroughly with water and then left in a drying cabinet until constant weight is reached. The compound can be purified by recrystallization from ethanol.

Yield: 9.4 g (80.3% of theory)

m.p.: 139°–141° C.

In the same way, from the corresponding α-formyl-carboxylic esters, the 4-substituted 1-thiocarbamoyl-5-hydroxypyrazoles listed in the following Table 1 can be obtained.

TABLE 1

$R^1 = R^2 = R^3 = H$

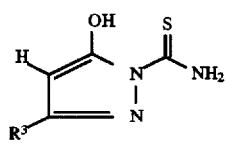

| Ex. No. | $R^4$ | m.p. |
|---|---|---|
| 1 | H— | |
| 2 | Me— | 164–165° C. |
| 3 | Et— | 144–145° C. |
| 4 | n-Pr— | 146–147° C. |
| 5 | i-Pr— | |
| 6 | c-Pr— | |

TABLE 1-continued $R^1 = R^2 = R^3 = H$

| Ex. No. | $R^4$ | m.p. |
|---|---|---|
| 7 | n-Bu— | 139–141° C. |
| 8 | i-Bu— | 128–131° C. |
| 9 | s-Bu— | |
| 10 | t-Bu— | |
| 11 | n-C₅H₁₁ | |
| 12 | Me₂CH-CH₂— | 153–154° C. |
| 13 | Me₂CH-CH(Me)— (branched) | |
| 14 | (Me)(Me)CH-CH(Me)-CH₂— | |
| 15 | Me₃C-CH₂— | |
| 16 | Me-CH=CH-CH(Me) | |
| 17 | Me₂CH-CH(Me)- | |
| 18 | Me-CH(Me)-CH=Me | |
| 19 | Me₂CH-CH₂-CH₂— | |
| 20 | Me₂C(Me)-CH₂-CH₂— | |
| 21 | Me-CH₂-CH(Me)-CH₂— | |
| 22 | Me-CH(Me)-CH(Me)-CH₂— | |
| 23 | Me-(CH₂)₃-CH₂— | 136–137° C. |
| 24 | Me₂CH-(CH₂)₂-CH₂ | |
| 25 | Me-CH(Me)-CH₂-CH₂— | |
| 26 | Me₂CH-CH(Me)-CH₃— | |

TABLE 1-continued $R^1 = R^2 = R^3 = H$

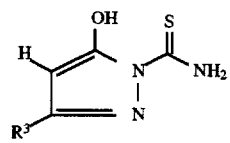

| Ex. No. | R⁴ | m.p. |
|---|---|---|
| 27 | Me-CH₂-CH₂-CH₂-CH(Me)-CH₂- | |
| 28 | Me-CH₂-CH₂-CH₂-CH₂-CH(Me)-CH₂- (isoheptyl) | |
| 29 | Me₂CH-CH₂-CH₂-CH₂-CH(Me)- | |
| 30 | cyclopropyl-CH₂-CH₂- | |
| 31 | cyclopropyl-CH₃ | |
| 32 | 1-F-cyclopropyl-CH₂- | |
| 33 | 1-Cl-cyclopropyl-CH₂- | |
| 34 | 1-CN-cyclopropyl-CH₂- | |
| 35 | NC—CH₂—CH₂— | |
| 36 | CF₃— | |
| 37 | CF₃—CH₂— | |
| 38 | CF₃—CF₂—CF₂— | |
| 39 | CF₂—CF₂—CH₂— | |
| 40 | CF₃—CF₂—CF₂—CH₂— | |
| 41 | CH₂=CH—CH₂— | 134–135° C. |
| 42 | Me₂C=CH—CH₂— | |
| 43 | Me—CH=CH—CH(Me)—CH₂— | |
| 44 | Me—C(Me)=C(Me)—CH₂— | |
| 45 | CH₂=C(Me)(Me)—CH₂— | |
| 46 | Me—CH=CH—CH(Me)—Me | |
| 47 | Me—CH=C(Me)—CH(Me)—Me | |

TABLE 1-continued $R^1 = R^2 = R^3 = H$

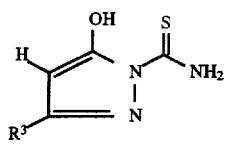

| Ex. No. | R⁴ | m.p. |
|---|---|---|
| 48 | Me₂C=C(Me)—CH(Me)— | |
| 49 | Me₂C=CH—CH₂—CH₂— | |
| 50 | Me—C(Me)=CH—CH₂—CH₂— *(shown with Me,Me/CH₂—)* | |
| 51 | Me—CH₂—C(Me)=CH—CH₂— | |
| 52 | Me₂C=CH—CH(Me)—CH₂— | |
| 53 | Me—CH=CH—CH₂—CH₂— | |
| 54 | Me₂C=CH—CH₂—CH₂—CH₂— | |
| 55 | Me—C(Me)=C(Me)—CH₂—CH₂— | |
| 56 | Me—CH₂—C(Me)=CH—CH₂—CH₂— | |
| 57 | Me—CH₂—CH₂—C(Me)=CH—CH₂— | |
| 58 | Me—CH₂—CH=CH—CH(Me)—Me | |
| 59 | Me—CH(Me)—CH=CH—CH(Me)—Me | |
| 60 | Me(Cl)C=CH—CH₂— | |
| 61 | Cl—CH=C(Cl)—CH₂— | |
| 62 | Cl₂C=C(Cl)—CH₂— | |
| 63 | Me(Cl)C=C(Me)(Me)—CH₂— | |

TABLE 1-continued $R^1 = R^2 = R^3 = H$

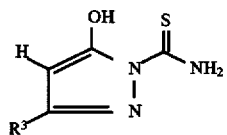

| Ex. No. | $R^4$ | m.p. |
|---|---|---|
| 64 | (Cl)(Me)C=C(Cl)CH(Me) — | |
| 65 | (Cl)(Cl)C=C(Cl)CH(Me) — | |
| 66 | (Cl)(Cl)C=CH—CH(Me) — | |
| 67 | (Cl)(Cl)C=CH—CH₂— | |
| 68 | (Cl)CH=C(Cl)—CH₂— | |
| 69 | (Me)CH=C(Cl)—CH(Me)CH₂— | |
| 70 | (Me)(Cl)C=C(Cl)—CH₂— | |
| 71 | (Me)(Cl)C=C(Cl)—CH₂CH₂— | |
| 72 | (Cl)(Cl)C=CH—CH₂CH₂CH₂— | |
| 73 | (Cl)CH=CH—CH(Cl)CH₂CH₂— | |
| 74 | (Me)CH₂—C(Cl)=C(Me)—CH₂— | |
| 75 | (Me)CH₂CH₂—C(Cl)=CH—CH₂— | |
| 76 | (Me)(Me)CH—CH₂CH₂—C(Cl)=CH(Me) | |
| 77 | (Me)(Me)C=CH—CH(Cl)CH₂CH₂— | |
| 78 | n-C₇H₁₅ | |

TABLE 1-continued $R^1 = R^2 = R^3 = H$

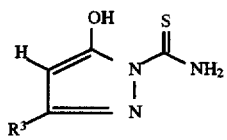

| Ex. No. | $R^4$ | m.p. |
|---|---|---|
| 79 | n-C₈H₁₇ | |
| 80 | n-C₉H₁₉ | |
| 81 | n-C₁₀—H₂₁ | 128–131° C. |
| 82 | n-C₁₁H₂₃ | |
| 83 | n-C₁₂H₂₅ | |
| 84 | n-C₁₃H₂₇ | |
| 91 | cyclohexyl | 157–158° C. |
| 92 | cyclohexenyl | |
| 93 | cyclohexyl-CH₂— | 185° C. |
| 94 | cyclohexenyl-CH₂— | |
| 95 | 3-(CO₂Et)-phenyl | 165–167° C. |
| 96 | phenyl | 176° C. |
| 97 | 2-Cl-phenyl | 231–236° C. |
| 98 | 3-Cl-phenyl | 168–169° C. |
| 99 | 4-Cl-phenyl | 231–232° C. |
| 100 | 2,4-di-Cl-phenyl | 171–173° C. |

TABLE 1-continued
$R^1 = R^2 = R^3 = H$
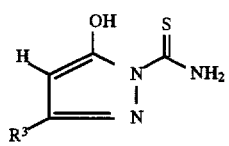
| Ex. No. | R⁴ | m.p. |
|---|---|---|
| 101 | 2,3-di-Cl-phenyl | |
| 102 | 3,4-di-Cl-phenyl | |
| 103 | 2,4-di-Cl-phenyl | |
| 104 | 2,6-di-Cl-phenyl | |
| 105 | 2-F-phenyl | 157–158° C. |
| 106 | 4-Br-phenyl | 194–195° C. |
| 107 | 5-F-2-Me-phenyl | 171–172° C. |
| 108 | 4-I-phenyl | |
| 109 | 2-CF₃-phenyl | 174–175° C. |
TABLE 1-continued
$R^1 = R^2 = R^3 = H$
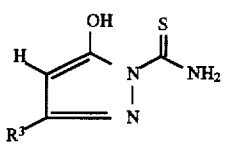
| Ex. No. | R⁴ | m.p. |
|---|---|---|
| 110 | 2-OMe-phenyl | 150° C. |
| 111 | 3-MeO-phenyl | 162–163° C. |
| 112 | 4-MeO-phenyl | 240–242° C. |
| 113 | 2,4-di-MeO-phenyl | |
| 114 | 2,3-di-MeO-phenyl | 263–265° C. |
| 115 | 2-MeO-4-Me-phenyl | 167° C. |
| 116 | 2-MeO-5-Me-phenyl | |
| 117 | 4-phenyl-phenyl | 284–286° C. |
| 118 | 2-phenyl-phenyl | |

TABLE 1-continued
$R^1 = R^2 = R^3 = H$
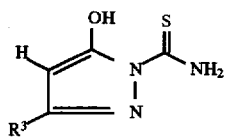
| Ex. No. | R⁴ | m.p. |
|---|---|---|
| 119 | 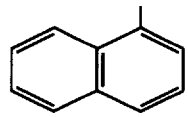 | 174–176° C. |
| 120 | 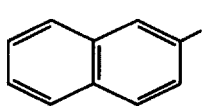 | 236–237° C. |
| 121 | 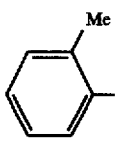 | 200° C. decomp. |
| 122 | 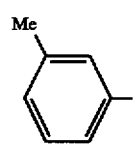 | 177° C. |
| 123 | 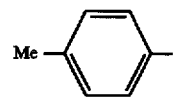 | 197–198° C. |
| 124 | 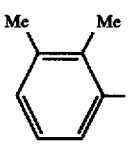 | |
| 125 | 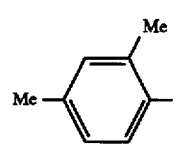 | 178–179° C. |
| 126 | 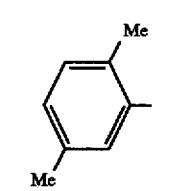 | |
| 127 | 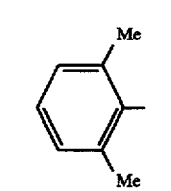 | |
TABLE 1-continued
$R^1 = R^2 = R^3 = H$
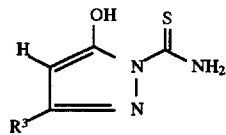
| Ex. No. | R⁴ | m.p. |
|---|---|---|
| 128 | 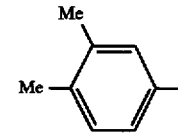 | |
| 129 | 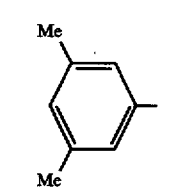 | |
| 130 | 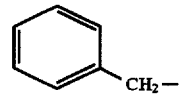 | 161–162° C. |
| 131 | 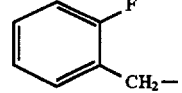 | 170–172° C. |
| 132 | 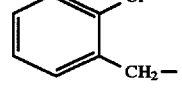 | 152–154° C. |
| 133 | 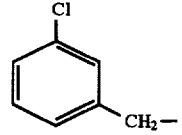 | 173° C. |
| 134 | 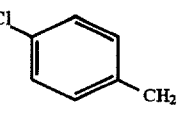 | 166–167° C. |
| 135 | 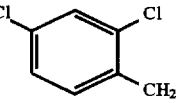 | 182° C. |
| 136 | 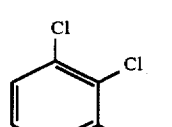 | 176° C. |
| 137 | 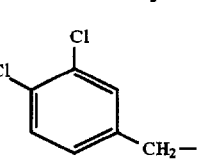 | |

TABLE 1-continued
$R^1 = R^2 = R^3 = H$
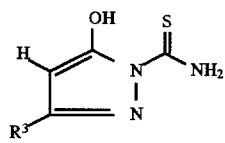
| Ex. No. | R⁴ | m.p. |
|---|---|---|
| 138 | 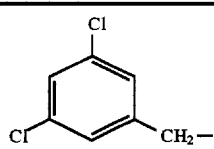 3,5-diCl-C₆H₃-CH₂- | |
| 139 | 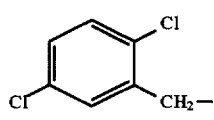 2,4-diCl-C₆H₃-CH₂- | |
| 140 | 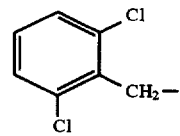 2,6-diCl-C₆H₃-CH₂- | |
| 141 | 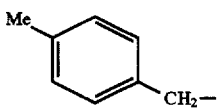 4-Me-C₆H₄-CH₂- | 186° C. |
| 142 | 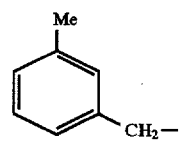 3-Me-C₆H₄-CH₂- | |
| 143 | 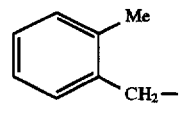 2-Me-C₆H₄-CH₂- | |
| 144 | 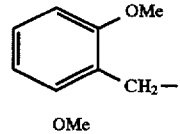 2-OMe-C₆H₄-CH₂- | |
| 145 | 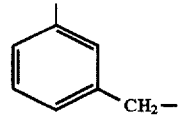 3-OMe-C₆H₄-CH₂- | |
| 146 | 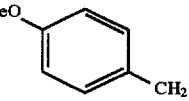 4-MeO-C₆H₄-CH₂- | 160° C. |
| 147 | 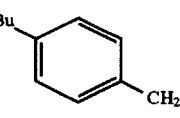 4-tBu-C₆H₄-CH₂- | >200° C. |
| 148 | 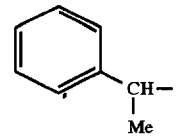 C₆H₅-CH(Me)- | 161–163° C. |
TABLE 1-continued
$R^1 = R^2 = R^3 = H$
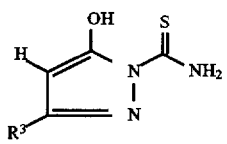
| Ex. No. | R⁴ | m.p. |
|---|---|---|
| 149 | 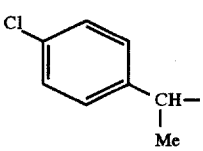 4-Cl-C₆H₄-CH(Me)- | |
| 150 | 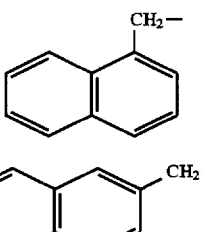 1-naphthyl-CH₂- | 169–170° C. |
| 151 | 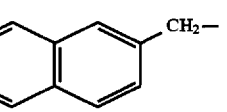 2-naphthyl-CH₂- | |
| 152 | 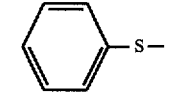 C₆H₅-S- | 213–214° C. |
| 153 | 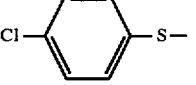 4-Cl-C₆H₄-S- | 207–208° C. |
| 154 | 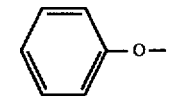 C₆H₅-O- | 204° C. |
| 155 | 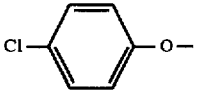 4-Cl-C₆H₄-O- | |
| 156 | 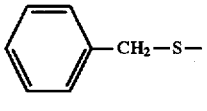 C₆H₅-CH₂-S- | 177–178° C. |
| 157 | 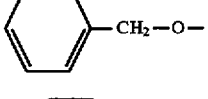 C₆H₅-CH₂-O- | 214° C. |
| 158 | 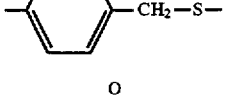 4-Cl-C₆H₄-CH₂-S- | |
| 159 | 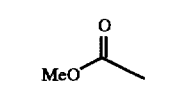 MeO-C(=O)- | |
| 160 | 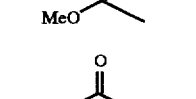 EtO-C(=O)- | 187° C. |

TABLE 1-continued $R^1 = R^2 = R^3 = H$

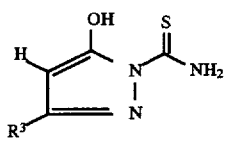

| Ex. No. | R⁴ | m.p. |
|---|---|---|
| 161 |   n-PrO-C(O)- | |
| 162 |   n-BuO-C(O)- | |
| 163 | Me—O— | 149–150° C. |
| 164 | Et—O— | |
| 165 | n-Pr—O— | |
| 166 | n-Bu—O— | |
| 167 | Me—S—CH₂— | |
| 168 | Et—S—CH₂— | |
| 169 | n-Pr—S—CH₂— | |
| 170 | n-Bu—S—CH₂— | |
| 171 | i-Pr—S—CH₂— | |
| 172 | n-C₅H₄—S—CH₂— | |
| 173 | Me—S—(CH₂)₂— | |
| 174 | Et—S—(CH₂)₂— | |
| 175 | n-Pr—S—(CH₂)₂— | |
| 176 | n-Bu—S—(CH₂)₂— | |
| 177 | Me—O—CH₂— | |
| 178 | Et—O—CH₂— | |
| 179 | n-Pr—O—CH₂— | |
| 180 | n-Bu—O—CH₂— | |
| 181 | n-Pr—O—CH₂— | |
| 182 | n-C₅H₄—O—CH₂— | |
| 183 | Me—O—(CH₂)₂— | |
| 184 | Et—O—(CH₂)₂— | |
| 185 | n-Pr—O—(CH₂)₂— | |
| 186 | n-Bu—O—(CH₂)₂— | |
| 187 | Ph—S—CH₂— | |
| 188 | Ph—O—CH₂— | |
| 189 | Ph—CH₂—S—CH₂— | |
| 190 | Ph—CH₂—O—CH₂— | |
| 191 | MeO-C(O)-CH₂— | |
| 192 | EtO-C(O)-CH₂— | 135–136° C. |
| 193 | 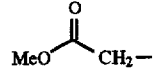 (4-F-C₆H₄—) | 145–6° C. |
| 194 | 2-furyl | |
| 195 | 2-thienyl | |
| 196 |  | |
| 197 |  | |
| 198 |  | |
| 199 | (5-Me-thien-2-yl) Me-thienyl | |
| 200 | Cl-pyrazolyl | 200° C. decomp. |
| 201 | 4-Br-C₆H₄—CH₂— | 170–171° C. |
| 202 | 2-Br-C₆H₄— | 162–163 |
| 203 | 4-F-C₆H₄— | 174–175° C. |
| 204 | 3-PhO-C₆H₄— | 148–149° C. |
| 205 | n-C₁₇—H₃₉ | 150–154° C. |
| 206 | EtO-C(O)-CH₂-CH₂— | |
| 207 | Me-CH₂-CH(Me)— | |

Example 4 from Table 2 (2/004)

(3-mono-substituted compounds)

4.6 g (0.05 mol) of thiosemicarbazide and 7.9 g (0.05 mol) of ethyl butyrylacetate together with 100 ml of ethanol are maintained at reflux temperature for 3 hours. The mixture is then left to cool to room temperature, and 5.9 g (0.05 mol, 97%) potassium tert-butylate are added in portions with stirring, after which stirring is continued at room temperature for 4 hours. The contents of the flask are then stirred into a mixture of 800 ml of water/50 ml of conc. HCl, and the resulting precipitate is filtered off with suction. After thorough washing with water the moist product is left in a drying cabinet (50 mbar/60° C.) until constant weight is reached.

Yield: 6.9 g (74.5% of theory)

m.p.: 160°–161° C., colourless solid.

In the same way, from the corresponding ethyl acylacetates, the 3-substituted 1-thiocarbamoyl-5-hydroxypyrazoles listed in the following Table 2 can be obtained.

The pyrazoles obtained are characterized by melting point determination.

TABLE 2

$R^1 = R^2 = R^4 = H$

| Ex. No. | $R^3$ | m.p. |
|---|---|---|
| 1 | H— | |
| 2 | Me— | 178° C. |
| 3 | Et— | 154–158° C. |
| 4 | n-Pr— | 160–161° C. |
| 5 | i-Pr— | 153° C. |
| 6 | c-Pr— | 158° C. |
| 7 | n-Bu— | 148° C. |
| 8 | i-Bu— | 153° C. |
| 9 | s-Bu— | 145–146° C. |
| 10 | t-Bu— | |
| 11 | n-C₅H₁₁ | 149° C. |
| 12 | Me₂CH-CH₂— | 151° C. |
| 13 | Me₂CH-CH(Me)-CH₂— | 142° C. |
| 14 | Me-CH(Me)-CH(Me)-CH₂— | |
| 15 | Me₃C-CH₂— | |
| 16 | Me-CH₂-CH(Me)-CH₂-Me | 137° C. |
| 17 | Me₂CH-CH(Me)-CH₂-Me | |
| 18 | Me-CH(Me)-CH₂-CH₂-Me | |
| 19 | Me₂CH-CH₂-CH₂-CH₂— | |

TABLE 2-continued $R^1 = R^2 = R^4 = H$

| Ex. No. | $R^3$ | m.p. |
|---|---|---|
| 20 | Me₂CH-CH₂-CH(Me)-CH₂— | |
| 21 | Me₂CH-CH₂-CH(Me)-CH₂— (isomer) | |
| 22 | Me-CH(Me)-CH₂-CH(Me)-CH₂— | |
| 23 | Me-(CH₂)₄-CH₂— | 142–143° C. |
| 24 | Me₂CH-CH₂-CH₂-CH₂-CH₂— | |
| 25 | Me-CH₂-CH(Me)-CH₂-CH₂-CH₂— | |
| 26 | Me-CH₂-CH(Me)-CH₂-CH₃— | |
| 27 | Me-CH₂-CH₂-CH(Me)-CH₂— | |
| 28 | Me-CH₂-CH₂-CH₂-CH(Me)₂ | |
| 29 | Me₂CH-CH₂-CH₂-CH(Me)₂ | |
| 30 | cyclopropyl-CH₂-CH₂— | |
| 31 | cyclopropyl-CH₃— | |
| 32 | (F-cyclopropyl)-CH₂— | |
| 33 | (Cl-cyclopropyl)-CH₂— | |
| 34 | (CN-cyclopropyl)-CH₂— | |
| 35 | NC—CH₂—CH₂— | |
| 36 | CF₃— | 87–88° C. |
| 37 | CF₃—CF₂— | |
| 38 | CF₃—CF₂—CF₂— | |
| 39 | CF₂—CF₂—CH₂— | |
| 40 | CF₃—CF₂—CF₂—CH₂— | |
| 41 | CH₂=CH-CH₂— | |

TABLE 2-continued $R^1 = R^2 = R^4 = H$

| Ex. No. | R³ | m.p. |
|---|---|---|
| 42 | Me₂C=CH-CH₂- | |
| 43 | Me₂CH-CH(Me)-CH₂- (isomer) | |
| 44 | Me₂C=C(Me)-CH₂- | |
| 45 | CH₂=C(Me)₂-C(Me)-CH₂- | |
| 46 | Me-CH=CH-CH(Me)- | |
| 47 | Me-CH=C(Me)-CH(Me)- | |
| 48 | Me-C(Me)=C(Me)-CH(Me)- | |
| 49 | Me₂C=CH-CH₂-CH₂- | |
| 50 | Me-CH=C(Me)-CH₂-CH₂- | |
| 51 | Me-CH=C(Me)-CH₂- (with ethyl) | |
| 52 | Me-CH=C(Me)-CH(Me)-CH₂- | |
| 53 | Me-CH=CH-CH₂-CH₂-CH₂- | |
| 54 | Me₂C=CH-CH₂-CH₂-CH₂- | |
| 55 | Me-CH=C(Me)-CH₂-CH₂-CH₂- | |
| 56 | Et-CH=C(Me)-CH₂-CH₂- | |
| 57 | Pr-CH=C(Me)-CH₂- | |
| 58 | Me-CH₂-CH=CH-CH(Me)-Me | |
| 59 | Me₂CH-CH=CH-CH(Me)-Me | |
| 60 | Me-C(Cl)=CH-CH₂-CH₂- | |
| 61 | Cl-CH=C(Cl)-CH₂-CH₂- | |
| 62 | Cl₂C=C(Cl)-CH₂-CH₂- | |
| 63 | Me-C(Cl)=C(Me)₂-CH₂- | |
| 64 | Me-C(Cl)=C(Cl)-CH(Me)- | |
| 65 | Cl₂C=C(Cl)-CH(Me)- | |
| 66 | Cl₂C=CH-CH(Me)-Me | |
| 67 | Cl₂C=CH-CH₂-CH₂- | |
| 68 | Cl-CH=C(Cl)-CH₂-CH₂- | |
| 69 | Me-CH=C(Cl)-CH(Me)-CH₂- | |
| 70 | Me-C(Cl)=C(Cl)-CH₂-CH₂- | |
| 71 | Me-CH₂-C(Cl)=C(Cl)-CH₂- | |

TABLE 2-continued $R^1 = R^2 = R^4 = H$

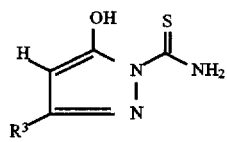

| Ex. No. | $R^3$ | m.p. |
|---|---|---|
| 72 | CCl₂=CH-CH₂-CH₂-CH₂- (1,1-dichloro) | |
| 73 | ClCH=CH-CHCl-CH₂-CH₂- | |
| 74 | Me-CH₂-C(Cl)=CH-CH₂- | |
| 75 | Me-CH₂-CH₂-C(Cl)=CH- | |
| 76 | Me-C(Cl)=CH-CH₂-CH(Me)- (with terminal Me) | |
| 77 | Me₂C=CH-CHCl-CH₂-CH₂- | |
| 78 | n-C₇H₁₅ | |
| 79 | n-C₈H₁₇ | 134–135° C. |
| 80 | n-C₉H₁₉ | |
| 81 | n-C₁₀H₂₁ | 154° C. |
| 82 | n-C₁₁H₂₃ | |
| 83 | n-C₁₂H₂₅ | |
| 84 | n-C₁₃H₂₇ | |
| 85 | cyclopentyl | 171° C. |
| 86 | cyclopentenyl | |
| 87 | cyclopentadienyl | |
| 88 | cyclopentyl-CH₂- | |
| 89 | cyclopentenyl-CH₂- | |
| 90 | cyclopentadienyl-CH₂- | |

TABLE 2-continued $R^1 = R^2 = R^4 = H$

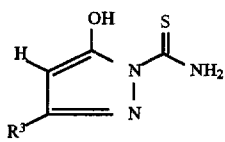

| Ex. No. | $R^3$ | m.p. |
|---|---|---|
| 91 | cyclohexyl | 154° C. |
| 92 | cyclohexenyl | |
| 93 | cyclohexyl-CH₂- | |
| 94 | cyclohexenyl-CH₂- | |
| 95 | 3-(CO₂Et)-phenyl | |
| 96 | phenyl | 142–143° C. |
| 97 | 2-Cl-phenyl | |
| 98 | 3-Cl-phenyl | |
| 99 | 4-Cl-phenyl | |
| 100 | 2,4-diCl-phenyl | |
| 101 | 2,3-diCl-phenyl | |

TABLE 2-continued
$R^1 = R^2 = R^4 = H$
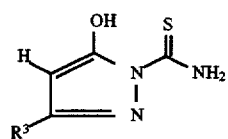
| Ex. No. | $R^3$ | m.p. |
|---|---|---|
| 102 | 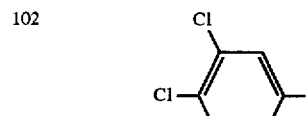 | |
| 103 | 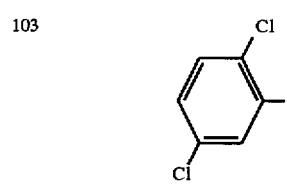 | |
| 104 | 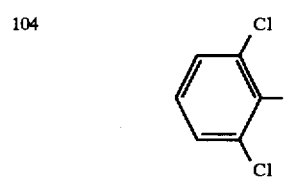 | |
| 105 | 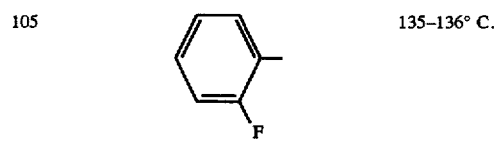 | 135–136° C. |
| 106 | 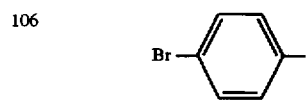 | |
| 107 | 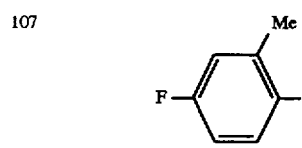 | |
| 108 | 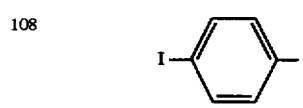 | |
| 109 | 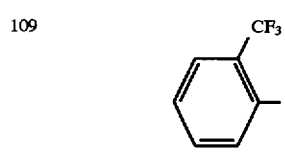 | |
| 110 | 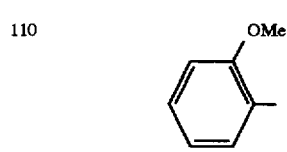 | |
TABLE 2-continued
$R^1 = R^2 = R^4 = H$
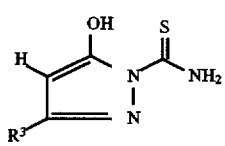
| Ex. No. | $R^3$ | m.p. |
|---|---|---|
| 111 | 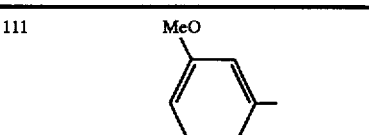 | |
| 112 | 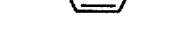 | |
| 113 | 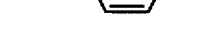 | |
| 114 | 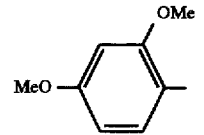 | |
| 115 | 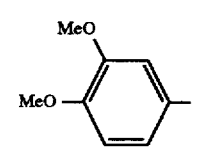 | |
| 116 | 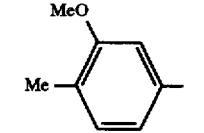 | |
| 117 | 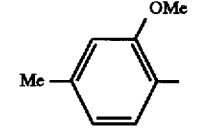 | |
| 118 | 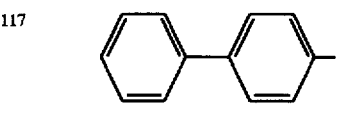 | |
| 119 | 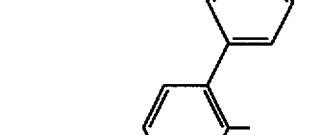 | |
| 120 | 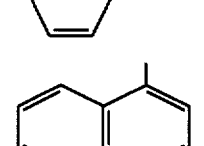 | |

TABLE 2-continued
R¹ = R² = R⁴ = H
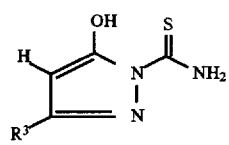
| Ex. No. | R³ | m.p. |
|---|---|---|
| 121 | 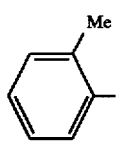 | |
| 122 | 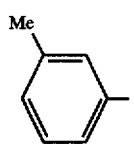 | |
| 123 | 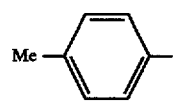 | |
| 124 | 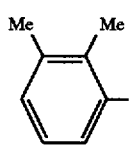 | |
| 125 | 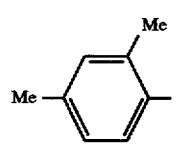 | |
| 126 | 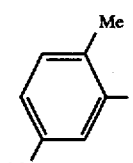 | |
| 127 | 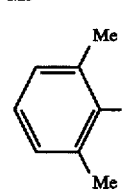 | |
| 128 | 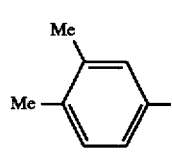 | |
| 129 | 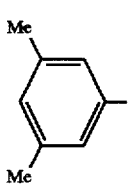 | |
TABLE 2-continued
R¹ = R² = R⁴ = H
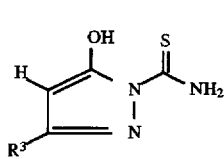
| Ex. No. | R³ | m.p. |
|---|---|---|
| 130 | 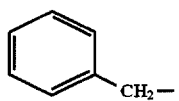 | |
| 131 | 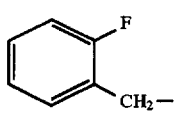 | |
| 132 | 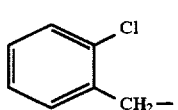 | |
| 133 | 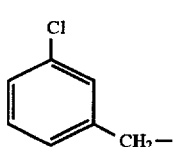 | |
| 134 | 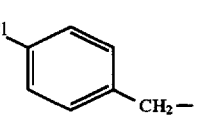 | |
| 135 | 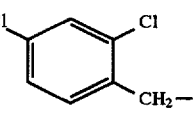 | |
| 136 | 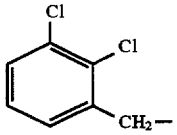 | |
| 137 | 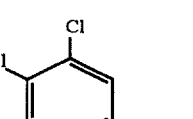 | |
| 138 | 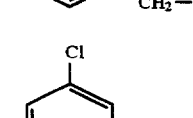 | |
| 139 | 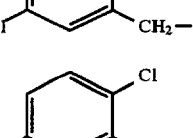 | |

TABLE 2-continued
$R^1 = R^2 = R^4 = H$
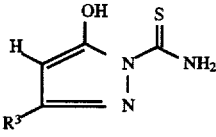
| Ex. No. | $R^3$ | m.p. |
|---|---|---|
| 140 | 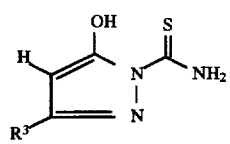 | |
| 141 | 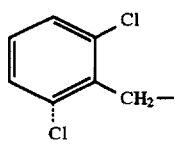 | |
| 142 | 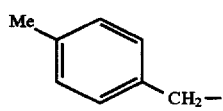 | |
| 143 | 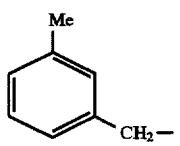 | |
| 144 | 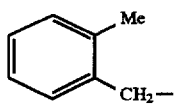 | |
| 145 | 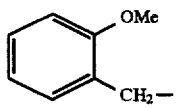 | |
| 146 | 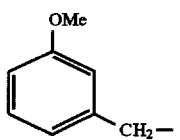 | |
| 147 | 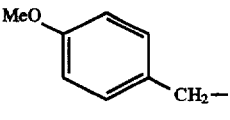 | |
| 148 | 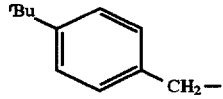 | |
| 149 | 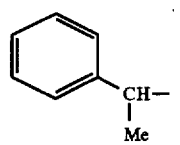 | |
| 150 | 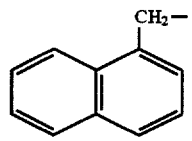 | |
| 151 | 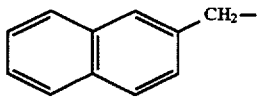 | |
| 152 | 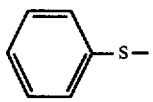 | |
| 153 |  | |
| 154 | 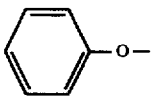 | |
| 155 | 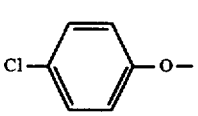 | |
| 156 | 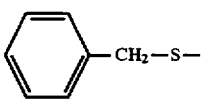 | |
| 157 | 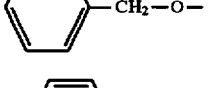 | |
| 158 | 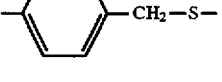 | |
| 159 | 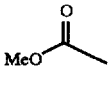 | |
| 160 | 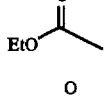 | |
| 161 | 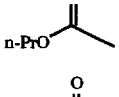 | |
| 162 | 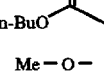 | |
| 163 | Me—O— | |

TABLE 2-continued $R^1 = R^2 = R^4 = H$

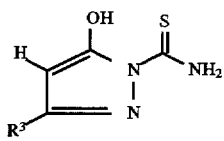

| Ex. No. | R³ | m.p. |
|---|---|---|
| 164 | Et—O— | |
| 165 | n-Pr—O— | |
| 166 | n-Bu—O— | |
| 167 | Me—S—CH₂— | |
| 168 | Et—S—CH₂— | 118–119° C. |
| 169 | n-Pr—S—CH₂— | |
| 170 | n-Bu—S—CH₂— | |
| 171 | i-Pr—S—CH₂— | |
| 172 | n-C₅H₄—S—CH₂ | |
| 173 | Me—S—(CH₂)₂— | |
| 174 | Et—S—(CH₂)₂— | |
| 175 | n-Pr—S—(CH₂)₂— | |
| 176 | n-Bu—S—(CH₂)₂— | |
| 177 | Me—O—CH₂— | |
| 178 | Et—O—CH₂— | |
| 179 | n-Pr—O—CH₂— | |
| 180 | n-Bu—O—CH₂— | |
| 181 | n-Pr—O—CH₂— | |
| 182 | n-C₅H₄—O—CH₂— | |
| 183 | Me—O—(CH₂)₂— | 140° C. |
| 184 | Et—O—(CH₂)₂— | |
| 185 | n-Pr—O—(CH₂)₂— | |
| 186 | n-Bu—O—(CH₂)₂— | |
| 187 | Ph—S—CH₂— | |
| 188 | Ph—O—CH₂— | 178.6° C. |
| 189 | Ph—CH₂—S—CH₂— | |
| 190 | Ph—CH₂—O—CH₂— | |
| 191 | MeO–C(O)–CH₂— | 142° C. |
| 192 | EtO–C(O)–CH₂— | 138° C. |
| 193 | 4-F-C₆H₄– | 145–6° C. |
| 194 | furan-2-yl | 152° C. |
| 195 | thiophen-2-yl | |
| 196 | 3-methylfuran-2-yl | |
| 197 | 3-methylthiophen-2-yl | |
| 198 | 2,5-dimethylfuran-3-yl | |

TABLE 2-continued $R^1 = R^2 = R^4 = H$

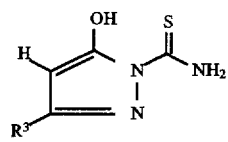

| Ex. No. | R³ | m.p. |
|---|---|---|
| 199 | 2,5-dimethylthiophen-3-yl | |
| 200 | Cl–CH=CH–N=N— | |
| 201 | 4-Br-C₆H₄–CH₂— | |
| 202 | 2-Br-C₆H₄— | |
| 203 | 4-F-C₆H₄— | |
| 204 | 3-phenoxyphenyl | |
| 205 | n-C₁₇—H₃₉ | |
| 206 | EtO–C(O)–CH₂CH₂–CH< | 130° C. |
| 207 | Me–CH₂–CH(Me)– | |

The numbering of the examples below follows the preceding Tables 1 and 2 and is composed of Table Number/Example Number.

EXAMPLES (3,4-disubstituted compounds)

Tables 3–8

Example 3 from Table 3

A mixture of 3.9 g (0.025 mol) of ethyl 2-ethyl-acetoacetate, acetate, 2.3 g (0.025 mol) of thiosemicarbazide and 100 ml of ethanol is held at reflux temperature for 3 hours with stirring. The reaction mixture is then cooled to 20° C., and 2.9 g (0.025 mol; 97%) of potassium tert-butylate are added in portions with stirring. The resulting suspension is then stirred for 3 hours at 20°–30° C. and subsequently stirred into dilute hydrochloric acid (500 ml of water/20 ml of conc. HCl), and the precipitate is filtered off with suction. It is washed thoroughly with water and dried under hot conditions until constant weight is reached.

Yield: 2.9 g (82.5% of theory)

m.p.: 163° C.

In the same way, from the corresponding α-substituted β-keto esters, the 3,4-disubstituted 1-thiocarbamoyl-5-hydroxypyrazoles listed in the following Tables 3–8 and 65 can be obtained.

TABLE 3

$R^1 = R^2 = H$
$R^3 = Me$
$R^4 =$ see Table 1

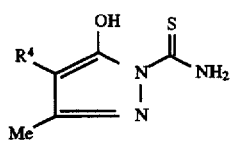

| | |
|---|---|
| 3/002 | m.p.: 164° C. |
| 3/035.H$_2$O | m.p.: 153° C. |
| 3/130 | m.p.: 160° C. |
| 3/148 | m.p.: 142–143° C. |
| 3/003 | m.p.: 163° C. |
| 3/007 | m.p.: 139° C. |
| 3/042 | m.p.: 148° C. |
| 3/078 | m.p.: 124° C. |
| 3/083 | m.p.: 112° C. |
| 3/023 | m.p.: 144° C. |
| 3/005 | m.p.: 137° C. |

TABLE 4

$R^1 = R^2 = H$
$R^3 =$ Table 1
$R^4 = Me$

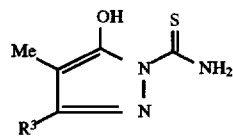

| | |
|---|---|
| 4/003 | m.p.: 152–153° C. |
| 4/004 | m.p.: 123° C. |
| 4/007 | m.p.: 131° C. |
| 4/011 | m.p.: 120° C. |

Table 5=Table 3 but $R^3$=Et

Table 6=Table 3 but $R^3$=n-Pr

Table 7=Table 4 but $R^4$=Et

Table 8=Table 4 but $R^4$=n-Pr

Tables 9 to 16 analogous to 1–8 but $R^1$=Me

Tables 17 to 32 analogous to 1–8 but $R^1=R^2$=Me

Tables 33 to 48 analogous to 1–8 but $R^1$=allyl

Tables 49 to 64 analogous to 1–8 but $R^1$=phenyl

| | | |
|---|---|---|
| 49/002 | m.p.: 204–205° C. | 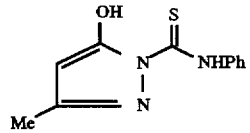 |
| 10/002 | m.p.: 210° C. decomp. | 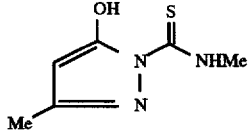 |
| 9/192 | m.p.: 176° C. | 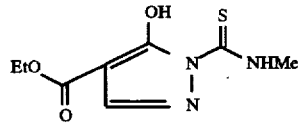 |
| 16/003 | m.p.: 74–75° C. | 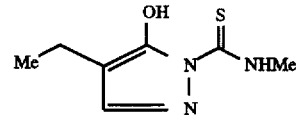 |
| 17/130 | m.p.: 181° C. | 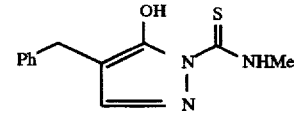 |

| | | |
|---|---|---|
| 11/023 | m.p.: 87–88° C. | 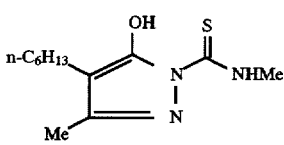 |
| 10/007 | m.p.: 147° C. | 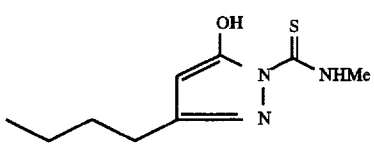 |
| 9/079 | m.p.: 117° C. | 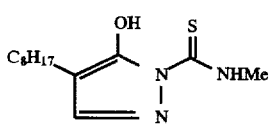 |
| 49/079 | m.p.: 153–156° C. | 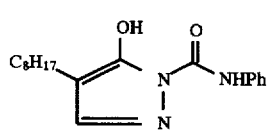 |
| 51/003 | m.p.: 175° C. | 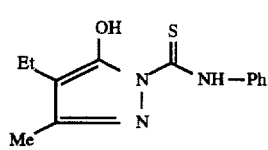 |
| 33/079 | m.p.: 71–72° C. | 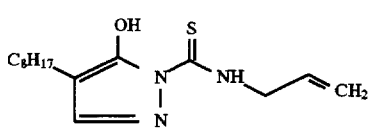 |
| 49/007 | m.p.: 209–210° C. | 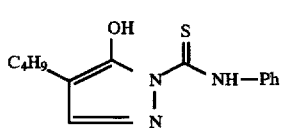 |
| 9/007 | m.p.: 134° C. | 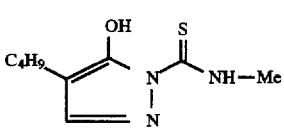 |
| 33/007 | m.p.: 80–81° C. | 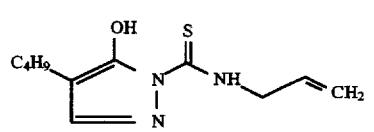 |
| 15/002 | m.p.: 153–154° C. | 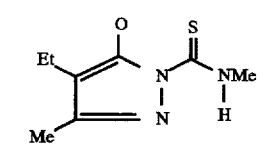 |
| 34/007 | m.p.: 92° C. | 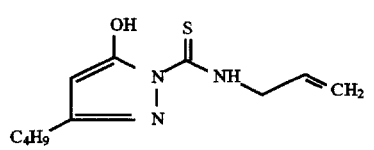 |

EXAMPLES FOR TABLE 65

If $R^3$ and $R^4$ represent a saturated chain, preparation is as for Tables 3 to 8; for unsaturated compounds derived from imidazolinone it is as follows:

13.8 g of ethyl 2-chloro-3,5-dinitrobenzoate, 60 ml of ethanol and 13.7 g of thiosemicarbazide are stirred at 25° C. for 54 h, and then, by filtering off the mother liquor with suction, 22 g of

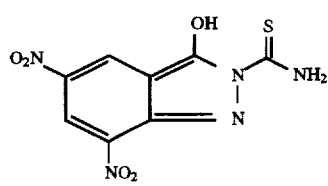

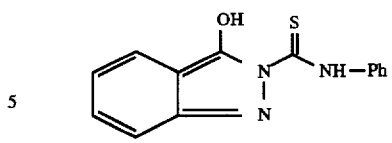

For compounds of this type, the keto form is also a particularly relevant species.

of melting point 153° C. are isolated, or 4.2 g of imidazolinone and 5.0 g of phenyl mustard oil are refluxed in toluene for 3 h and the crystals which separate out on cooling are isolated: 0.6 g, m.p.=194° C., decomposition.

Table 65

$R^3$ and $R^4$ form a ring
$R^1$ and $R^2$: see Examples

| | | |
|---|---|---|
| 65/001 | 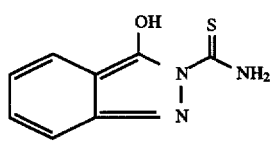 | |
| 65/002 | 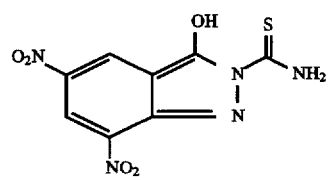 | m.p.: 153° C. |
| 65/003 | 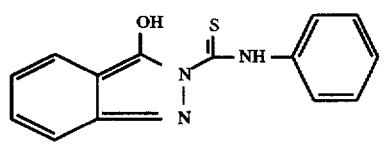 | m.p.: 194° C. (decomp.) |
| 65/004 | 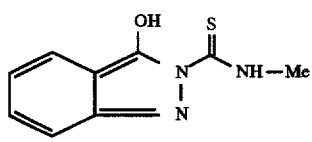 | m.p.: 199° C. |
| 65/006 | 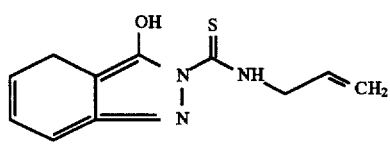 | m.p.: 160° C. |
| 65/007 | 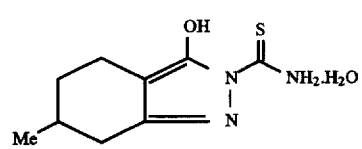 | m.p.: 173° C. |
| 65/008 | 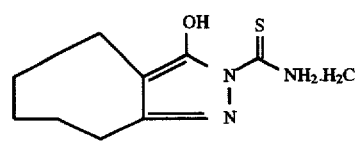 | m.p.: 148° C. |

-continued

| | | |
|---|---|---|
| 65/009 | 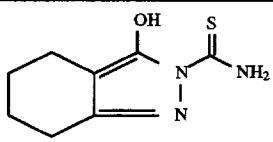 | m.p.: 179–180° C. |
| 65/010 | 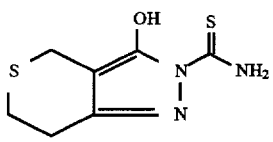 | m.p.: 102–103° C. |
| 65/011 | 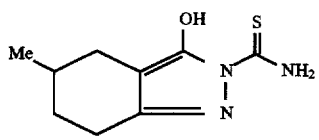 | m.p.: 176° C. |

Tables 66–130

As Tables 1–65, but in each case complexes with metals; see Examples

| | | |
|---|---|---|
| 66/007 | 2H$_2$O.1/2 Zn | m.p.: 189–192° C. |
| 66/130 | 1/2 Zn | m.p.: 160° C. |
| 66/007 | 1/2 Zn | m.p.: 178–180° C. |

Preparation of compounds from Tables 131–139:

EXAMPLE NO. 131/007

10.0 g (0.05 mol) of 86% ethyl α-formyl-hexanoate and 5.3 g (0.05 mol) of thiocarbohydrazide are refluxed for 3.5 hours in 100 ml of ethanol, and subsequently 5.8 g (0.05 mol) of potassium tert-butylate are added at 25° C. After stirring overnight, evaporation of the solvent in a rotary evaporator and addition of 200 ml of water, filtration with suction is carried out, the filtrate is drawn up with suction, and filtration with suction is repeated.

1.0 g of 131/007 is obtained with a melting point of 116°–118° C.

Tables 131–139

As Tables 1–8 or 65, but with the following basic structure:

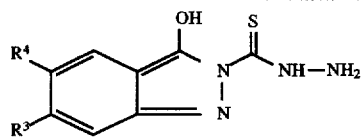

| | |
|---|---|
| 131/007 m.p.: 116–118° C. | 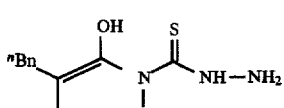 |
| 133/007 m.p.: 160–165° C. | 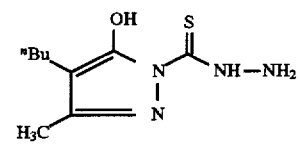 |
| 139/009 m.p.: 129–130° C. | 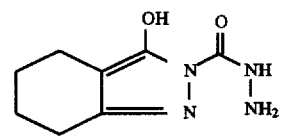 |

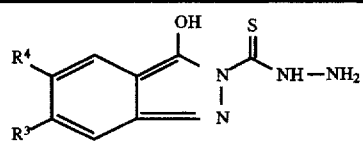

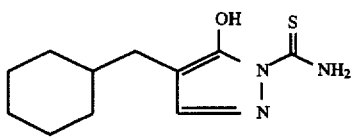

PREPARATION EXAMPLES FOR COMPOUNDS OF FORMULA Ia

Example 1a

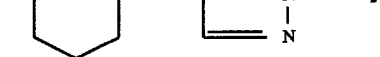

76.0 g of ethyl 3-cyclohexylpropionate are initially introduced into 200 ml of dimethylformamide at 0° to 5° C., and 24.6 g of sodium hydride (80% strength in oil) are added. After dropwise addition of 235 ml of ethyl formate, the mixture is stirred at 25° C. for 24 hours. The batch is stirred into 1.6 l of 10% strength HCl, extracted with 800 ml of methylene chloride and distilled. 34.2 g (41%) of ethyl 2-formyl-3-cyclohexylpropionate of boiling point 91°–95° C./1.25 mm are obtained.

10.6 g of the oil obtained were heated under reflux in 150 ml of ethanol with 4.55 g of thiosemicarbazide for 4 hours. 5.6 g of potassium tert-butylate were added at 25° C. and the mixture was stirred for 24 hours. After introduction into 600 ml of 10% strength HCl, 7.8 g (66%) of the target compound of melting point 185° C. are obtained after recrystallization from ethanol.

Example 2a

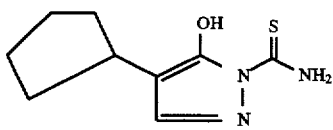

8 g of ethyl 2-formyl-2-cyclopentylacetate, prepared from the commercial 2-cyclopenteneacetic acid by esterification and formylation by known methods, were refuxed for 4 hours in 70 ml of ethanol with 3.9 g of thiosemicarbazide, 4.8 g of potassium tert-butylate were added, and the mixture was allowed to stand for about 12 hours. Pouring onto ice/10% HCl gives 2.5° C. of the target compound of melting point m.p.: 160° C.

Example 3a

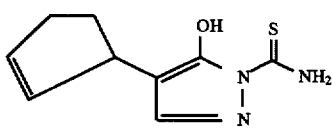

Analogously to Example 1a, the compound of melting point m.p. 152° C. is obtained.

Example 4a

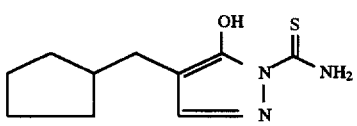

40.7 g of ethyl 3-cyclopentylpropionate are placed in 400 ml of DMF at from 0° to 5° C., 14.4 g of sodium hydride (80% in oil) are added. After dropwise addition of 200 ml of ethyl formate, the mixture is stirred at 25° C. for 24 h. The mixture is stirred into 1.6 l of 10% HCl, extracted with 800 ml of methylene chloride and distilled. 19.7 g (41%) are obtained of ethyl 2-formyl-3-cyclopentylpropionate of boiling point 117° C./12 min.

9.7 g of the oil obtained were heated under reflux in 80 ml of ethanol with 4.47 g of thiosemicarbazide for 4 h, 5.5 g of potassium tert-butylate were added at 25° C., and the mixture was stirred for 24 h. The mixture was then introduced into 250 ml of 10% HCl to give, after recrystallization from ethanol, 5 g (45%) of the target compound of melting point 157° C.

Testing of the mould resistance of paint films

The substance to be tested for its fungicidal activity is incorporated in the desired concentration into the (emulsion) paint by means of a dissolver. The paint is then brushed onto both sides of a suitable substrate.

To obtain results relevant in practice, some of the test specimens are leached out with running water (24 hours; 20° C.) before the test for mould resistance.

The test specimens prepared in this way are placed on an agar nutrient medium. The test specimens and nutrient medium are contaminated with species of fungi. After storage at 29°±1° C. and 80 to 90% relative atmospheric humidity for 1 to 3 weeks, the samples are compared. The paint film is permanently mould-resistant if the test specimen remains free from fungus or at most a slight attack at the edge can be detected.

Fungal spores of the following nine mould fungi, which are known as destroyers of paint films or are often encountered on paint films, are used for the contamination:
1. Alternaria tenuis
2. Aspergillus flavus
3. Aspergillus niger
4. Aspergillus ustus
5. Cladosporium herbarum
6. Paecilomyces variotii
7. Penicillium citrinum
8. Aureobasidium pullulans
9. Stachybotrys atra Corda The following table shows the active compound concentrations at which the paint film test specimen remains free from fungus (concentrations based on the solids content of the emulsion paint).

Example 4a:

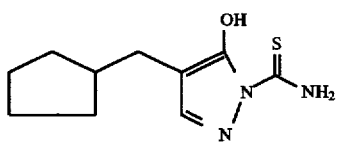

Example 2a:

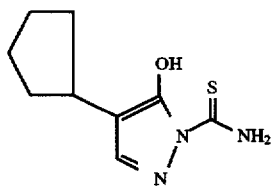

TABLE

|  | No exposure | After water treatment | Discolouration |
|---|---|---|---|
| Example 4a | 1.5% | >2% | none |
| Example 2a | 0.6% | 1.5% | none |
| Example 1a | 0.6% | 0.6% | none |

It will be appreciated that the instant specification and the claims are set forth by way of illustration and not limitation, and that various modifications and changes may be made without departing from the spirit and scope of the present invention.

We claim:

1. A thiocarbamoyl compound of the formula

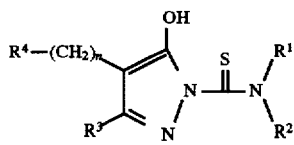

(Ia)

in which $R^1$, $R^2$ and $R^3$ in each case independently of one another represent hydrogen or methyl and $R^4$ represents cyclopentyl n represents the number 1 or a metal salt complex or an acid addition product thereof.

2. A compound according to claim 1, in which $R^1$, $R^2$ and $R^3$ represent hydrogen.

3. A process for the protection of industrial materials against attack or destruction by undesirable microorganisms, which comprises applying or mixing a compound according to claim 1 to the materials to be protected.

4. A composition for the protection of industrial material, which comprises at least one compound according to claim 1.

5. A process for the preparation of a compound of

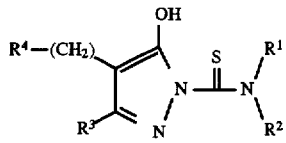
(Ia)

$R^1$, $R^2$ and $R^3$ in each case independently of one another represent hydrogen or methyl and $R^4$ represents cyclopentyl, cyclopentenyl, or cyclohexenyl, which comprises reacting a formyl acid derivative of the formula

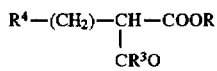
(II)

wherein $R^3$ and $R^4$ are defined above and R represents methyl, ethyl, n- or i-propyl or n-, i-, s- or t-butyl, with a thiosemicarbazido of the formula

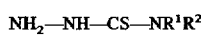
(III)

optionally in the presence of a diluent or solvent and a base.

6. A thiocarbamoyl compound of the formula

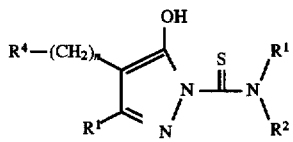
(Ia)

in which $R^1$, $R^2$ and $R^3$ in each case independently of one another represent hydrogen or methyl and $R^4$ represents cyclopentenyl or cyclohexenyl, n represents 0 or 1 or a salt or metal complex thereof.

7. A compound according to claim 6, in which $R^1$, $R^2$ and $R^3$ represent hydrogen.

8. A process for the protection of industrial materials against attack or destruction by undesirable microorganisms, which comprises applying or mixing a compound according to claim 6 to the materials to be protected.

9. A composition for the protection of industrial material, which comprises at least one compound according to claim 6.

10. The compound according to claim 6, which has the formula

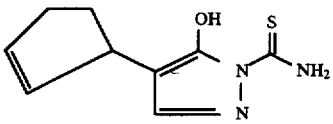

or a metal salt complex or an acid addition product thereof.

11. The compound according to claim 6, which has the formula

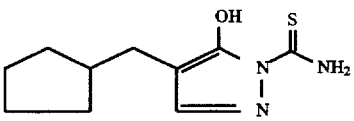

or a metal salt complex or an acid addition product thereof.

12. A process for the protection of industrial materials against attack or destruction by undesired microorganism which comprises applying or mixing a compound of the formula

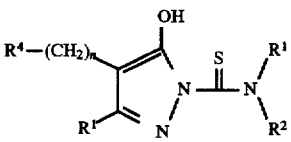
(Ia)

in which $R^1$, $R^2$ and $R^3$ in each case independently of one another represent hydrogen or methyl, $R^4$ represents cyclohexyl, n represents 1, or a metal salt complex or an acid addition salt thereof.

13. The process according to claim 12, wherein the compound is

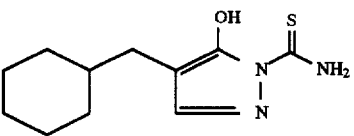

or a metal salt complex or an acid addition salt thereof.

* * * * *

UNITED STATES PATENT AND TRADEMARK OFFICE
CERTIFICATE OF CORRECTION

PATENT NO. : 5,672,617
DATED : September 30, 1997
INVENTOR(S) : Peter Wachtler et al It is certified that error appears in the above-identified patent and that said Letters Patent is hereby corrected as shown below:

Column 53, Claim 5, Line 30      Delete "thiosemicarbazido" and insert --thiosemicarbazide--

Signed and Sealed this

Twenty-fourth Day of October, 2000

Attest:

Q. TODD DICKINSON

*Attesting Officer*      *Director of Patents and Trademarks*